United States Patent [19]

Theodoridis

[11] Patent Number: 5,262,390
[45] Date of Patent: Nov. 16, 1993

[54] HERBICICAL 2-[(4-HETEROCYCLIC-PHENOXYMETHYL)-PHENOXY]-ALKANOATES

[75] Inventor: George Theodoridis, Princeton, N.J.

[73] Assignee: FMC Corporation, Philadelphia, Pa.

[21] Appl. No.: 935,601

[22] Filed: Aug. 26, 1992

[51] Int. Cl.$^5$ ............... A01N 43/653; C07D 249/12
[52] U.S. Cl. ........................ 504/273; 548/263.2;
548/263.4; 548/267.6; 548/267.8; 548/269.4
[58] Field of Search ............ 548/263.2, 267.6, 267.8,
548/269.4; 71/92; 504/273

[56] References Cited
U.S. PATENT DOCUMENTS 5,084,085  1/1992  Theodoridis ..................... 71/92

Primary Examiner—Mukund J. Shah
Assistant Examiner—Y. N. Gupta
Attorney, Agent, or Firm—H. Robinson Ertelt; Robert M. Kennedy

[57] ABSTRACT

Herbicidal compounds, compositions containing them, and a method for controlling weeds by application of the compositions are disclosed. The herbicidal compounds are 2-[4-heterocyclic(phenoxymethyl)phenoxy-y]alkanoates of the formula

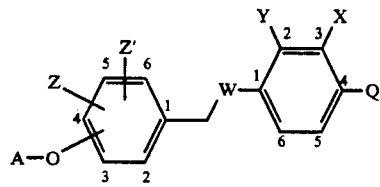

in which A is a derivative of an alkanoate bonded to the phenoxy oxygen at the alpha carbon, and Q is 4-difluoromethyl-4,5-dihydro-3-methyl-1,2,4-triazol-5(1H)-on-1-yl, 3,4,5,6-tetrahydrophthalimid-1-yl, 1-(1-methylethyl)imidazolidin-2,4-dion-3-yl, 1,4-dihydro-4-(3-fluoropropyl)-5H-tetrazol-5-on-1-yl, 3-chloro-4,5,6,7-tetrahydroindazol-2-yl, 4-methyl-1,2,4-triazine-3,5-dion-2-yl, 8-thia-1,6-diazabicyclo[4.3.0]nonane-7-on-9-ylimino, or 1-methyl-6-trifluoromethyl-2,4-pyrimidinedione-3-yl; X is hydrogen, fluorine, or chlorine; Y is hydrogen; W is oxygen or sulfur; Z is hydrogen, fluorine, chlorine, bromine, lower alkyl, or methoxy; Z' is hydrogen, fluorine, or chlorine; and the group AO— may be in the 2, 3, or 4-position of the phenyl ring.

13 Claims, No Drawings

HERBICICAL 2-[(4-HETEROCYCLIC-PHENOXYMETHYL)-PHENOXY]-ALKANOATES

This invention pertains to novel herbicidal 2-[(4-heterocyclic-substituted-3-halophenoxymethyl)phenoxy]alkanoates, especially propionates and acetates, and their use for weed control in agriculture, horticulture, and other fields in which it is desired to control unwanted plant growth, such as grassy or broadleaf plant species. In particular, it pertains to those compounds in which the heterocyclic moiety is selected from among 4-difluoromethyl-4,5-dihydro-3-methyl-1,2,4-triazol-5(1H)-on-1-yl, 3,4,5,6-tetrahydrophthalimid-1-yl, 1-(1-methylethyl)imidazolidin-2,4-dion-3-yl, 1,4-dihydro-4-(3-fluoropropyl)-5H-tetrazol-5-on-1-yl, 3-chloro-4,5,6,7-tetrahydroindazol-2-yl, 4-methyl-1,2,4-triazine-3,5-dion-2-yl, 8-thia-1,6-diazabicyclo[4.3.0]nonane-7-on-9-ylimino, and 1-methyl-6-trifluoromethyl-2,4-pyrimidinedione-3-yl groups. These compounds are both pre- and postemergence herbicides. The use of this class of compounds as herbicides has not previously been described.

U.S. Pat. No. 5,084,085 discloses compounds of the formula:

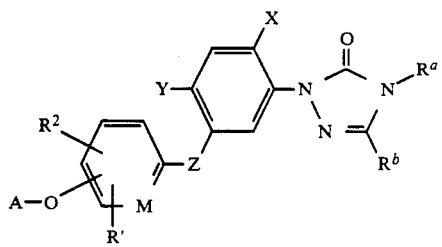

wherein $R^a$ is preferably lower haloalkyl, and $R^b$ is preferably lower alkyl;

$R'$ and $R^2$ are broadly defined;

X and Y are independently halogen, alkyl, alkoxy, alkylthio, haloalkyl, nitro, cyano, sulfonylalkyl, or —SOCF$_3$;

M is CH or N; and

A is a derivative of an alkanoate bonded to the phenoxy oxygen at the alpha carbon.

U.S. Pat. No. 4,816,065 discloses compounds like those of U.S. Pat. No. 5,084,085, except that the triazolinone ring has been replaced by a 3,4,5,6-tetrahydrophthalimido moiety. Similarly, U.S. Pat. No. 4,885,025 discloses compounds in which the triazolinone ring of U.S. Pat. No. 5,084,085 has been replaced with a tetrazolinone moiety.

U.S. Pat. No. 3,984,434, Japanese patents 54-25018, 54-6534, and 60-39668, and Japanese patent applications 49-000432 and 54-19965, all assigned to Mitsubishi Chemical Industries, Ltd., disclose compounds of the general formula:

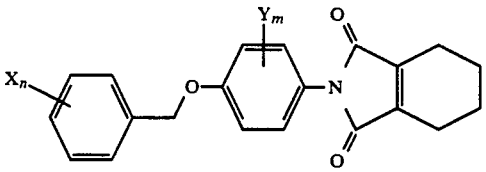

wherein

X is hydrogen, halogen, nitro, alkyl, or alkoxy,

Y is hydrogen, halogen, alkyl, and n and m are each 1 to 4.

It has now been found that 2-[(4-heterocyclic-substituted-3-halophenoxymethyl)phenoxy]alkanoates are unexpectedly active as both pre- and postemergence herbicides. In particular, as preemergence herbicides many of these compounds exhibit tolerance of soybeans and, to a certain extent, of corn. Perhaps of greater interest is the postemergence activity, where no crop tolerance is exhibited, making them excellent candidates as total vegetation control agents.

The novel 2-[(4-heterocyclic-substituted-3-halophenoxymethyl)phenoxy]alkanoates of the present invention are described by the following generic structure:

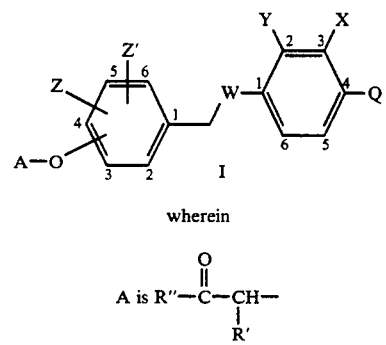

wherein

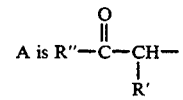

Q is selected from the following heterocycles:

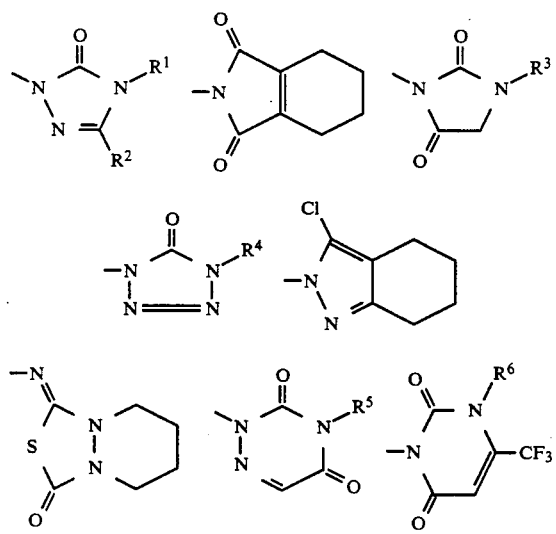

W is oxygen or sulfur;
X is selected from hydrogen, fluorine, or chlorine;
Y is hydrogen, or X and Y taken together may be —O—C(CH$_3$)$_2$CH$_2$— to form a 7-substituted-4-benzofuranyl moiety;

R' is hydrogen or methyl;

R" is —OR or amino, arylamino (e.g. phenylamino), alkylamino (e.g. lower alkylamino such as methylamino or dimethylamino), alkenylamino (e.g. lower alkenylamino such as diallylamino), alkoxyamino (e.g. lower alkoxyamino such as methoxyamino), cyano, or alkyl-, haloalkyl-, or arylsulfonylamino of the formula —N(lower alkyl)SO$_2$R$^9$, or —NHSO$_2$R$^9$;

R is hydrogen, M, alkyl (e.g., lower alkyl such as methyl or ethyl), cycloalkyl, lower alkenyl or lower alkynyl (such as allyl or propargyl), or —[CHR$^7$(CH$_2$)$_m$O]$_n$R$^8$, each of R$^1$ through R$^6$ is lower alkyl or lower haloalkyl;

R$^7$ is hydrogen or lower alkyl;

R$^8$ is alkyl, preferably lower alkyl;

R$^9$ is alkyl (e.g. lower alkyl such as methyl, ethyl or propyl), haloalkyl (e.g. halo lower alkyl such as trifluoromethyl), or aryl such as phenyl or substituted phenyl, (e.g. lower alkoxy-substituted and/or halo-substituted phenyl);

m is 0 to 2, preferably 0 to 1, and n is 1 to 6, preferably 1 to 3; and

M is a monovalent, salt-forming group such as sodium, potassium, or ammonium;

Z is hydrogen, fluorine, chlorine, bromine, lower alkyl, phenyl, or methoxy;

Z' is hydrogen, fluorine, or chlorine; or

Z and Z' taken together may be —(CH$_2$)$_4$— to form a tetrahydronaphthyl moiety; and the group A—O— may be in the 2, 3, or 4-position of the phenyl ring.

Preferred compounds are those in which R" is —OR, X is fluorine or chlorine, and Z is chlorine or lower alkyl.

Particularly preferred are those compounds in which R is lower alkyl or —[CHR$^7$(CH$_2$)$_m$O]$_n$R$^8$; R$^1$ is difluoromethyl; R$^2$ is methyl; R$^3$ is 1-methylethyl; R$^4$ is 3-fluoropropyl; R$^5$ is methyl; R$^6$ is methyl; R$^7$ is H or CH$_3$; R' is methyl; Z is in the 4-position; Z' is hydrogen or chlorine in the 3-position; m is 0 or 1, and n is 1 to 3; and the group AO— is in the 2-position of the phenyl ring.

Many of the compounds of the invention were prepared by the following reaction:

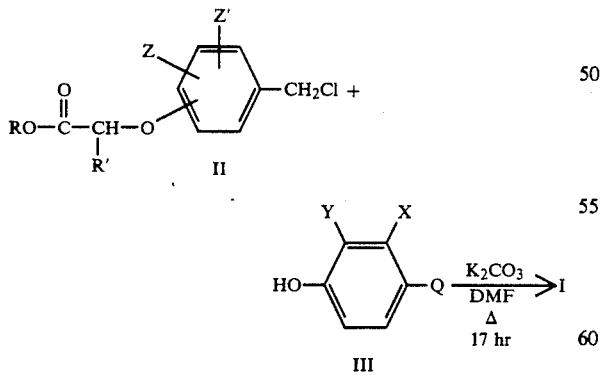

An appropriately substituted methyl 2-(chloromethylphenoxy)alkanoate and an appropriately substituted 4-heterocyclic-substituted phenol were heated in N,N-dimethylformamide at 80° C. in the presence of at least a molar equivalent of potassium carbonate. Usually the reaction was run overnight. Preparation of the corresponding acid (R=H) was accomplished by hydrolyzing the ester with aqueous sodium hydroxide and then acidifying the product with hydrochloric acid. For those compounds in which R is 2-(2-methoxyethoxy)ethyl, transesterification of the methyl ester with 2-(2-methoxyethoxy)ethanol in the presence of titanium (IV) isopropoxide was utilized.

Intermediates were prepared according to the following schemata:

SCHEMA A

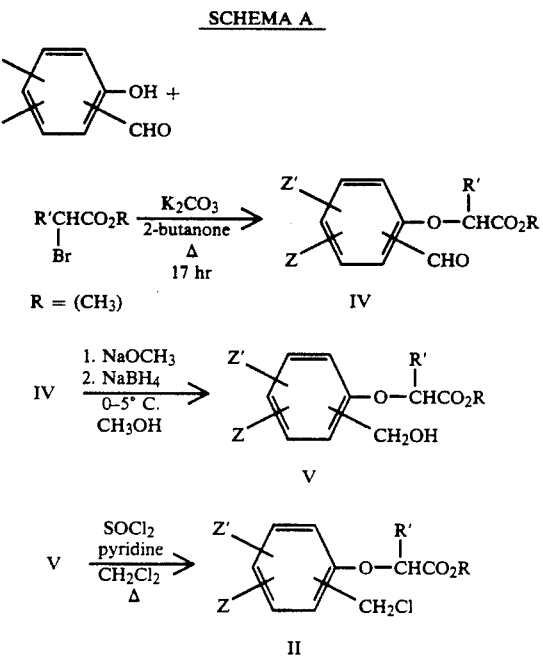

Thus, a mixture of an appropriately substituted formyl-substituted phenol and a methyl 2-bromoalkanoate was heated at 70° C. in 2-butanone in the presence of potassium carbonate. Usually the reaction was run overnight, producing the corresponding 2-(substituted formylphenoxy)alkanoate (IV). This compound was then reduced with sodium methoxide and sodium borohydride in methanol, yielding the corresponding 2-(hydroxymethylphenoxy)alkanoate (V). Reaction of V with thionyl chloride in methylene chloride in the presence of a catalytic amount of pyridine produced the corresponding 2-(chloromethylphenoxy)alkanoate (II).

SCHEMA B

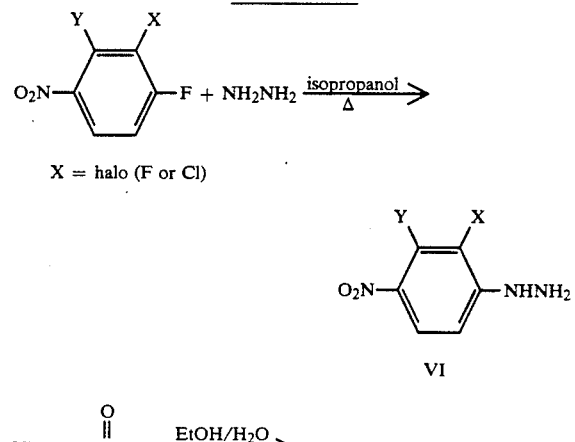

-continued
SCHEMA B

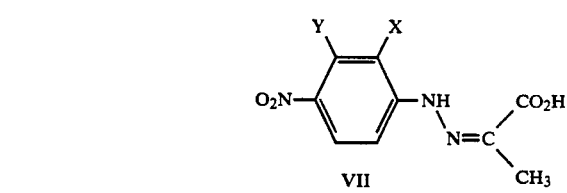

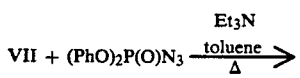

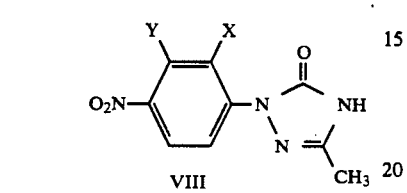

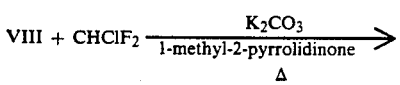

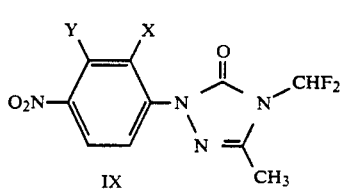

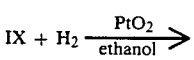

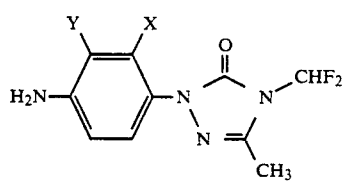

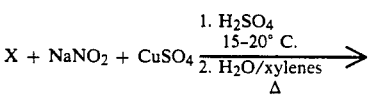

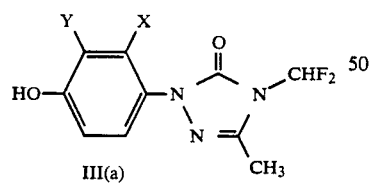

To prepare compounds of the invention in which Q is 4-difluoromethyl-4,5-dihydro-3-methyl-1,2,4-triazol-5(1H)-on-1-yl, a 3-halo-4-fluoronitrobenzene was reacted with hydrazine in isopropanol at reflux, preparing the corresponding 2-halo-4-nitrophenylhydrazine (VI). Reaction of VI with pyruvic acid in ethanol and water produced the 2-halo-4-nitrophenylhydrazone of pyruvic acid (VII). Preparation of the triazolinone ring was accomplished by heating VII with diphenylphosphoryl azide and triethylamine in toluene at reflux, producing 1-(2-halo-4-nitrophenyl)-4,5-dihydro-3-methyl-1,2,4-triazol-5(1H)-one (VIII). Chlorodifluoromethane was then reacted with VIII and potassium carbonate in 1-methyl-2-pyrrolidinone by heating the mixture at 120° C., producing 1-(2-halo-4-nitrophenyl)-4-difluoromethyl-3-methyl-1,2,4-triazol-5(1H)-one (IX). Hydrogenation of IX in ethanol using platinum oxide as catalyst produced 1-(4-amino-2-halophenyl)-4,5-dihydro-4-difluoromethyl-3-methyl-1,2,4-triazol-5(1H)-one (X). Preparation of intermediate III (a) was completed by reaction of X with sodium nitrite in sulfuric acid and subsequently with copper (II) sulfate in the presence of iron (II) sulfate in a mixture of water and xylenes.

SCHEMA C

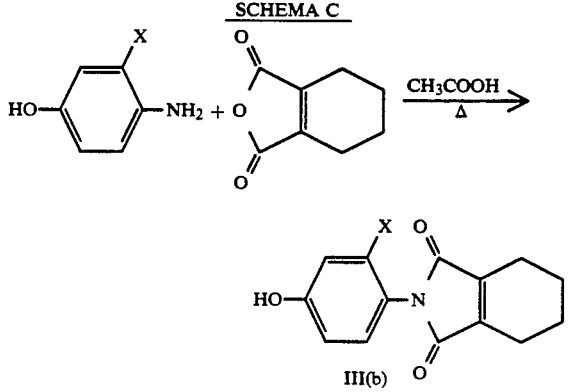

To prepare the tetrahydrophthalimide-substituted intermediate (III(b)), an appropriately substituted 4-aminophenol was refluxed with tetrahydrophthalic anhydride, producing the corresponding N-(4-hydroxy-substituted-phenyl)tetrahydrophthalimide.

SCHEMA D

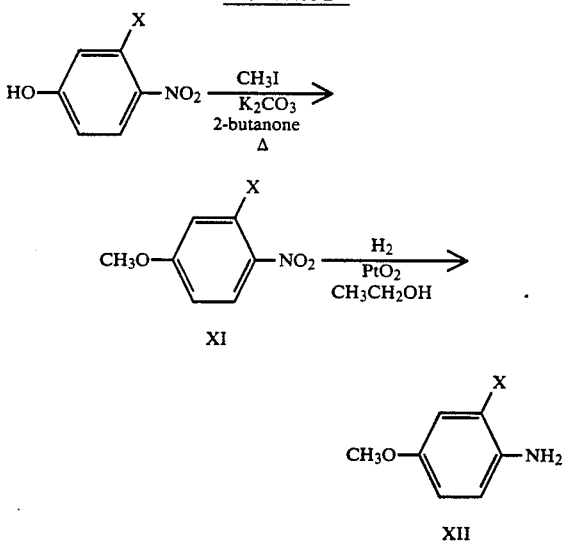

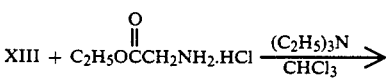

-continued
SCHEMA D

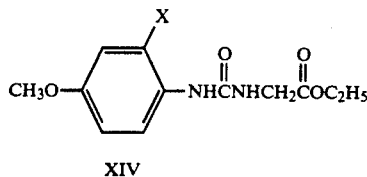

XIV

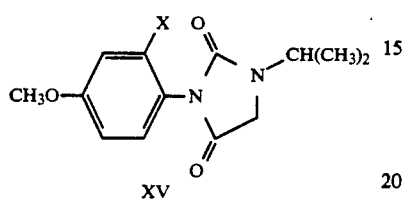

XV

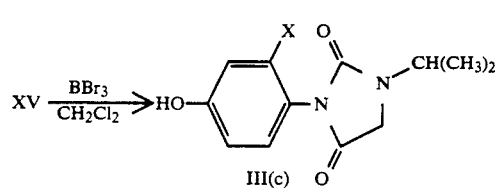

III(c)

An appropriately substituted 4-nitrophenol was heated with methyl iodide in the presence of potassium carbonate in 2-butanone to prepare the corresponding substituted 4-nitroanisole (XI). Compound XI was hydrogenated over platinum oxide, producing a substituted 4-methoxyaniline (XII). The reaction of XII with trichloromethyl chloroformate prepared the corresponding substituted 4-methoxyphenyl isocyanate (XIII). Reaction of this isocyanate with the ethyl ester of glycine hydrochloride and triethylamine in chloroform yielded N-(4-methoxy-substituted-phenyl)-N'-ethoxycarbonylmethylurea (XIV). Sequentially, XIV was reacted with sodium hydride and then with 2-iodopropane, yielding ultimately 1-(1-methylethyl)-3-(4-methoxy-substituted-phenyl)imidazolidin-2,4-dione (XV). Cleavage of the methoxy group of XV with boron tribromide yielded intermediate III (c).

SCHEMA E

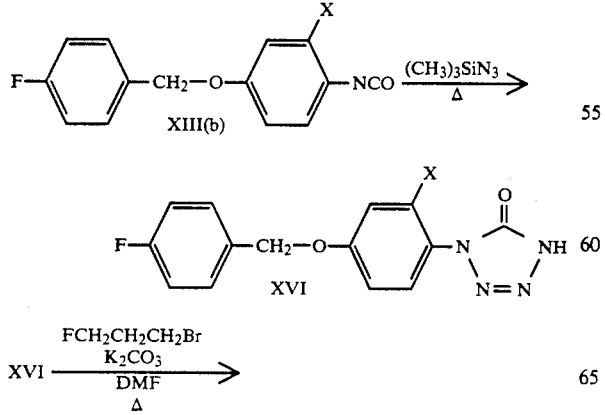

-continued
SCHEMA E

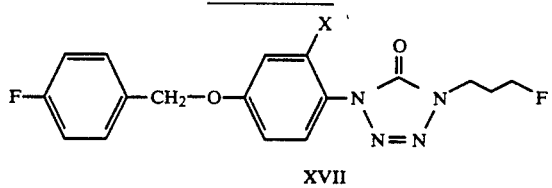

XVII

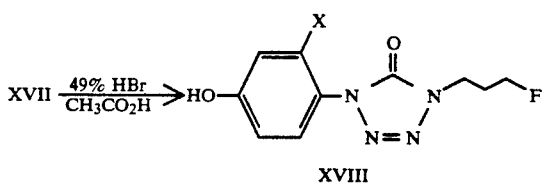

XVIII

An appropriately substituted phenyl isocyanate (XIII(b)) was prepared by the first three steps of Schema D and then was reacted with trimethylsilyl azide to prepare the correspondingly substituted phenyl-substituted tetrazolinone (XVI). After this tetrazolinone was alkylated in the 4-position with 1-bromo-3-fluoropropane to make the 3-fluoropropyl-substituted compound (XVII), the 4-fluorobenzyl protecting group was removed with 49% hydrobromic acid in acetic acid, yielding the desired hydroxy-substituted intermediate (XVIII).

SCHEMA F

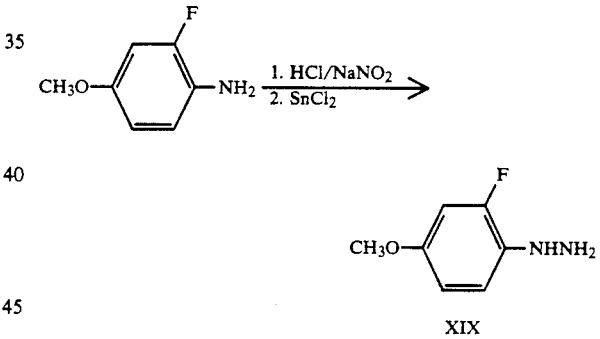

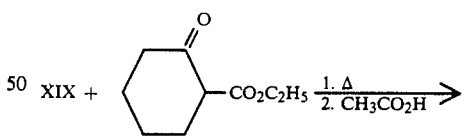

XIX

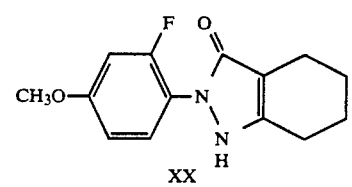

XX

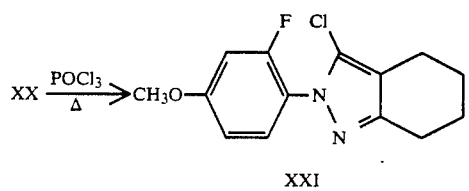

XXI

-continued
SCHEMA F

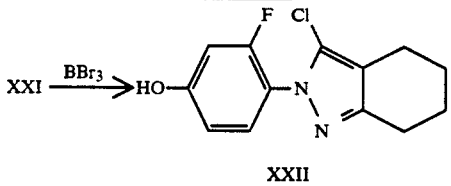

The diazonium salt of 2-fluoro-4-methoxyaniline was prepared using sodium nitrite and hydrochloric acid and was then reduced in situ with tin(II) chloride to prepare the correspondingly substituted phenylhydrazine (XIX). Reaction of this hydrazine with ethyl 2-cyclohexanonecarboxylate and subsequent heating of the product in the presence of acetic acid produced a mixture of 2-(2-fluoro-4-methoxyphenyl)-4,5,6,7-tetrahydro-1H-indazol-3-one (XX) and the 2-fluoro-4-methoxyphenylhydrazone of 2-cyclohexanonecarboxylic acid. This mixture was heated in phosphorus oxychloride, yielding 3-chloro-2-(2-fluoro-4-methoxyphenyl)-4,5,6,7-tetrahydroindazole (XXI), which was then cleaved with boron tribromide to the desired 3-chloro-2-(2-fluoro-4-hydroxyphenyl)-4,5,6,7-tetrahydroindazole (XXII).

SCHEMA G

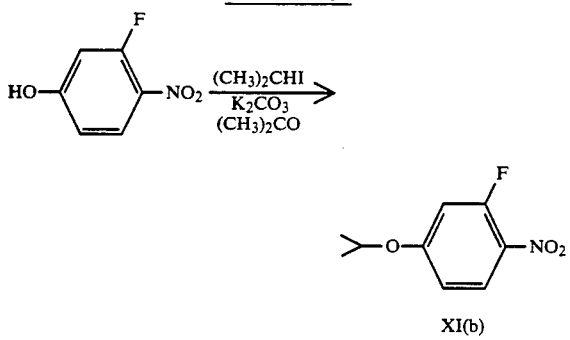

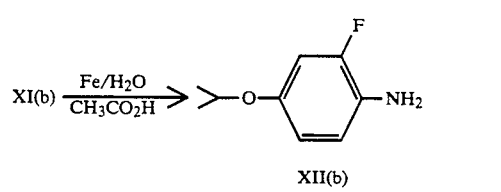

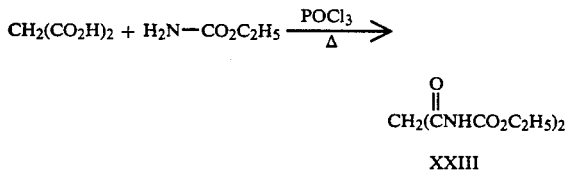

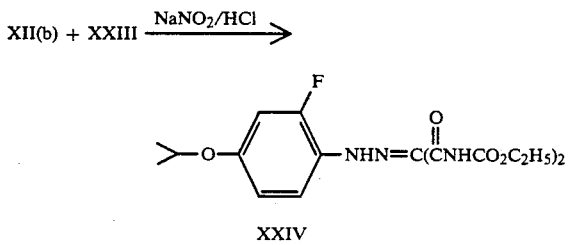

-continued
SCHEMA G

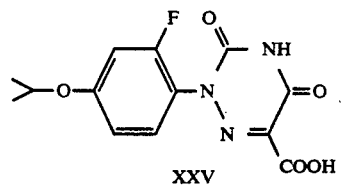

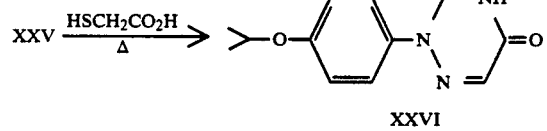

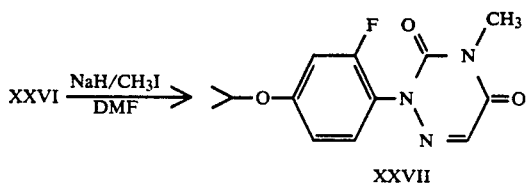

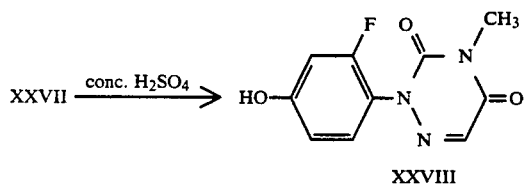

Etherification of 3-fluoro-4-nitrophenol with isopropyl iodide in the presence of potassium carbonate produced 2-fluoro-4-isopropoxynitrobenzene (XI(b)), which was reduced to 2-fluoro-4-isopropoxyaniline (XII(b)) with iron in aqueous acetic acid. Malonic acid was reacted with urethane (ethyl carbamate) in phosphorus oxychloride to produce malonyldiurethane (XXIII). The reaction of XII(b) and XXIII was effected by sodium nitrite and hydrochloric acid, producing 2-(4-isopropoxy-2-fluorophenyl)hydrazonomalonyldiurethane (XXIV), which was cyclized with sodium hydroxide to the corresponding 2-(substituted phenyl)-1,2,4-triazine-3,5-dion-6-carboxylic acid (XXV). Decarboxylation of XXV with thioglycolic acid and heat yielded XXVI which was then methylated at the 4-position with sodium hydride and methyl iodide producing the corresponding 2-(substituted phenyl)-4-methyl-1,2,4-triazine-3,5-dione (XXVII). In the final step the isopropyl protecting group was cleaved from the molecule with concentrated sulfuric acid, producing the desired hydroxy-substituted intermediate (XXVIII).

SCHEMA H

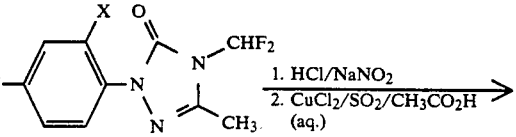

-continued
SCHEMA H

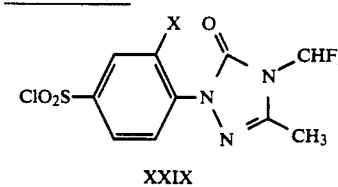
XXIX

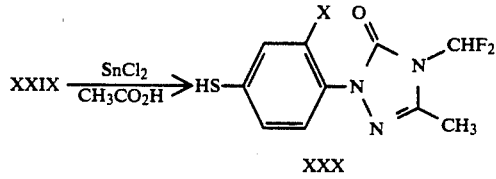
XXX

Preparation of the mercapto analog of intermediate III(a) started with intermediate X, which was converted to the corresponding diazonium salt. This diazonium compound was immediately reacted with copper (II) chloride and sulfur dioxide in aqueous acetic acid, producing the corresponding substituted phenylsulfonyl chloride (XXIX). Reduction of the sulfonyl chloride moiety to a thiol group was effected using tin (II) chloride in acetic acid, yielding, for example, 4-(4-difluoromethyl-4,5-dihydro-3-methyl-1,2,4-triazol-5(1H)-on-1-yl)-3-fluorothiophenol (XXX), the desired intermediate.

SCHEMA I

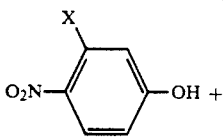

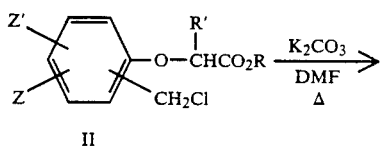
II

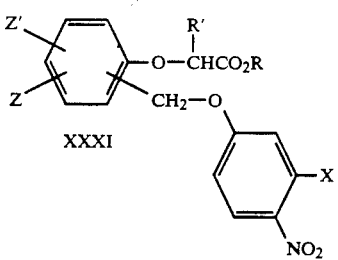
XXXI

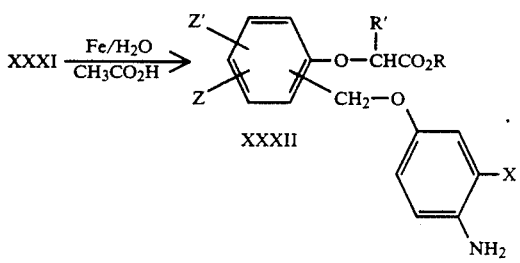
XXXII

-continued
SCHEMA I

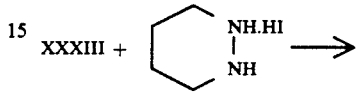
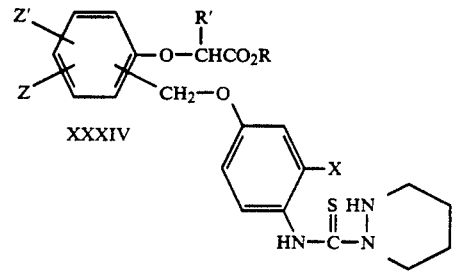
XXXIII

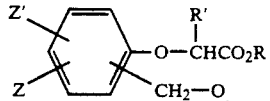
XXXIII +

XXXIV

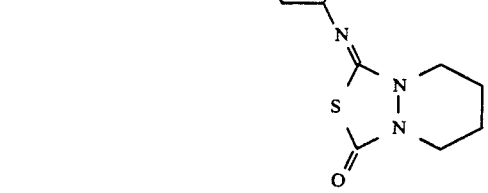
XXXV

Unlike the preparation of the other heterocyclic-substituted herbicidal compounds of this invention, where the final step is the reaction of II and III to form the herbicide, in the preparation of the compounds in which Q is 8-thia-1,6-diazabicyclo[4.3.0]nonane-7-on-9-ylimino II and II are first reacted to form an intermediate prior to forming the heterocycle. Thus, II was reacted with 3-fluoro-4-nitrophenol in N,N-dimethylformamide in the presence of potassium carbonate, yielding a 2-(4-nitrophenoxymethylphenoxy)alkanoate (XXXI). Reduction of XXXI with iron and water in acetic acid produced the corresponding amino compound (XXXII), which was then converted to the isothiocyanate (XXXIII) with thiophosgene and trimethylamine. Perhydropyridazine monohydroiodide and XXXIII were then reacted, forming a 2-(4-perhydropyridazin-1-ylthiocarbonylaminophenoxymethylphenoxy]alkanoate (XXXIV). Cyclization of XXXIV using trichloromethyl chloroformate and triethylamine yielded, for example, methyl 2-[2-[4-(8-thia-1,6-diazabicyclo[4.3.0]nonane-7-on-9-ylimino)-3-fluorophenoxymethyl]-5-methylphenoxy]propionate (XXXV), the desired herbicidal compound.

Similarly, the compounds in which Q is 1-methyl-6-trifluoromethyl-2,4-pyrimidinedione-3-yl may be prepared by the method of Schema I through the preparation of XXXII. Then XXXII is converted to the isocyanate with phosgene in place of thiophosgene, and the isocyanate is reacted with ethyl 3-amino-4,4,4-trifluoro-2-butenoate to yield the desired herbicidal compound.

In this specification "lower alkyl" contains 1 to 6 carbons, preferably 1 to 4, "lower alkenyl" or "lower alkynyl" contains 2 to 6 carbons, preferably 2 to 4, "cycloalkyl" contains 3 to 6 carbons, and "halogen" or "halo" means bromine, chlorine, or fluorine, preferably chlorine or fluorine.

The methods for preparing the novel herbicidal compounds of the invention are exemplified below.

All NMR spectra are reported as proton assignments in ppm in $CDCl_3$.

EXAMPLE 1

METHYL 2-[2-[4-(4-DIFLUOROMETHYL-4,5-DIHYDRO-3-METHYL-1,2,4-TRIAZOL-5(1H)-ON-1-YL)-3-FLUOROPHENOXYMETHYL]-5-METHYL-PHENOXY]PROPIONATE (Compound 12)

Step A: 2-Fluoro-4-nitrophenylhydrazine

To a solution of 20.0 g (0.126 mole) of 3,4-difluoronitrobenzene in 50 mL of isopropyl alcohol was slowly added a solution of 4.04 g (0.126 mole) of hydrazine in 20 mL of isopropyl alcohol, causing the reaction mixture to become orange. Upon completion of addition, the reaction mixture was heated at reflux for 30 minutes. A yellow solid, m.p. 137°-139° C., was filtered from the reaction mixture. The NMR spectrum of this solid was consistent with 2-fluoro-4-nitrophenylhydrazine. This product was used in Step B without being fully dried, assuming a 100% yield.

Step B: 2-Fluoro-4-nitrophenylhydrazone of pyruvic acid

A thick mixture of 21.6 g (0.126 mole) of wet 2-fluoro-4-nitrophenylhydrazine (Step A) in 100 mL of ethanol and 11.27 g (0.128 mole) of pyruvic acid in 20 mL of water were mixed. After the reaction mixture had stirred for 20 minutes, it was filtered to yield 15.5 g of a yellow solid, m.p. 210° C. (decomposition). An NMR spectrum of the product was consistent with the structure of the 2-fluoro-4-nitrophenylhydrazone of pyruvic acid. This reaction was repeated to obtain additional product.

Step C: 1-(2-Fluoro-4-nitrophenyl)-4,5-dihydro-3-methyl-1,2,4-triazol-5(1H)-one

A mixture of 29.62 g (0.123 mole) of the 2-fluoro-4-nitrophenylhydrazone of pyruvic acid, 12.45 g (0.123 mole) of triethylamine, and 33.85 g (0.123 mole) of diphenylphosphoryl azide in 200 mL of toluene was heated slowly to reflux. Heating at reflux was continued for two hours during which this yellow mixture became an orange solution. After cooling to room temperature, the reaction mixture was extracted with a solution of 17.0 g (0.425 mole) of sodium hydroxide in 200 mL of water. The aqueous extract was separated and was almost completely neutralized with concentrated hydrochloric acid. Just before pH 7 was reached, dry ice was added to the solution, completing the neutralization and causing a brown solid to precipitate. Filtration of this mixture yielded 26.15 g of 1-(2-fluoro-4-nitrophenyl)-4,5-dihydro-3-methyl-1,2,4-triazol-5(1H)-one as a brown solid, m.p. 211°-212° C. The NMR spectrum was consistent with the proposed structure.

Step D: 1-(2-Fluoro-4-nitrophenyl)-4-difluoromethyl-4,5-dihydro-1,2,4-triazol-5(1H)-one A mixture of 5.0 g (0.025 mole) of 1-(2-fluoro-4-nitrophenyl)-4,5-dihydro-3-methyl-1,2,4-triazol-5(1H)one and 29.0 g (0.210 mole) of dry, ground potassium carbonate in 200 mL of 1-methyl-2-pyrrolidinone was heated at 120° C. for 30 minutes. Chlorodifluoromethane was bubbled into the reaction mixture for five minutes. Thin layer chromatography of the reaction mixture revealed that the reaction had not gone to completion. Therefore, chlorodifluoromethane was bubbled into the reaction mixture for an additional three minutes. The reaction mixture was poured over ice and then was neutralized with concentrated hydrochloric acid. This mixture was extracted twice with diethyl ether. The combined extracts were washed with water, dried over anhydrous magnesium sulfate, and filtered. The filtrate was evaporated under reduced pressure, leaving a dark brown solid residue. This solid was dissolved in 100 mL of acetic acid and 5 mL of hydrobromic acid, and this solution was heated at reflux for one hour. This mixture was poured over ice and was then extracted with ethyl acetate. This extract was washed twice with water, dried over anhydrous magnesium sulfate, and filtered. The filtrate was evaporated under reduced pressure, leaving a black oil as a residue. This residue was put on a silica gel column and eluted with methylene chloride/ethyl acetate (97.5/2.5). After the product-containing fractions had been combined, the solvents were evaporated under reduced pressure, leaving 4.6 g of 1-(2-fluoro-4-nitrophenyl)-4-difluoromethyl-4,5-dihydro-3-methyl-1,2,4-triazol-5(1H)-one as a residue, m.p. 72°-77° C. The NMR spectrum was consistent with the proposed structure.

This reaction was repeated to obtain additional 1-(2-fluoro-4-nitrophenyl)-4-difluoromethyl-4,5-dihydro-3-methyl-1,2,4-triazol-5(1H)-one for the remainder of the synthesis.

Step E: 1-(2-Fluoro-4-aminophenyl)-4-difluoromethyl-4,5-dihydro-3-methyl-1,2,4-triazol-5(1H)-one A mixture of 24.5 g (0.085 mole) of 1-(2-fluoro-4-nitrophenyl)-4-difluoromethyl-4,5-dihydro-3-methyl-1,2,4-triazol-5(1H)-one and 0.30 g of platinum oxide in 250 mL of absolute ethanol was hydrogenated in a Parr hydrogenation apparatus. The calculated amount of hydrogen required was taken up in 45 minutes. The reaction mixture was filtered through a Buchner funnel, and the filtrate was evaporated under reduced pressure, leaving a dark brown solid residue. This residue was placed on a silica gel column and eluted with methylene chloride/ethyl acetate (75/25). After the product-containing fractions were combined, evaporation of the solvents under reduced pressure yielded 20.1 g of 1-(2-fluoro-4-aminophenyl)-4-difluoromethyl-4,5-dihydro-3-methyl-1,2,4-triazol-5(1H)-one. The NMR spectrum was consistent with the proposed structure.

Step F: 1-(2-Fluoro-4-hydroxyphenyl)-4-difluoromethyl-4,5-dihydro-3-methyl-1,2,4-triazol-5(1H)-one A solution of 20.0 g (0.0774 mole) of 1-(2-fluoro-4-aminophenyl)-4-difluoromethyl-4,5-dihydro-3-methyl-1,2,4-triazol-5(1H)-one in 100 mL of concentrated sulfuric acid was cooled to 15°–20° C. A solution of 5.3 g (0.0774 mole) of sodium nitrite in 20 mL of water was added slowly to the sulfuric acid solution while the temperature was maintained between 15° C. and 20° C. The dark orange solution was stirred for an hour at this temperature. The solution was then added rapidly to a solution of 250 g (1.00 mole) of copper (II) sulfate pentahydrate and 2.0 g (0.0072 mole) of iron (II) sulfate heptahydrate in 250 mL of water and 250 mL of mixed xylenes. This two-phase solution was heated at reflux for one hour, after which it was cooled and the phases separated. The organic layer was dried over anhydrous magnesium sulfate and filtered. The filtrate was evaporated under reduced pressure, leaving a brown oil. The aqueous layer was extracted with ethyl acetate, and the extract was dried over anhydrous magnesium sulfate and then filtered. The extract was combined with the brown oil from the organic phase, and the solvent was evaporated under reduced pressure, again leaving a brown oil. This brown oil was placed on a silica gel column and eluted with methylene chloride/ethyl acetate (90/10). The product-containing fractions were combined, and the solvent was evaporated under reduced pressure, leaving 12.17 g of 1-(2-fluoro-4-hydroxyphenyl)-4-difluoromethyl-4,5-dihydro-3-methyl-1,2,4-triazol-5(1H)-one, m p. 112°–114° C. The NMR spectrum was consistent with the proposed structure.

Step G: 4-Methylsalicylaldehyde

A 1M solution of ethylmagnesium bromide in tetrahydrofuran (100 ml) was cooled to 15° C., and a solution of 10.81 g (0.100 mole) of m-cresol was added during a 45 minute period while the temperature was held at 15° C. Upon completion of the addition, the mixture was stirred at room temperature for 30 minutes, and then a mixture of 7.5 g (0.25 mole) of paraformaldehyde and 17.92 g (0.100 mole) of hexamethylphosphoramide in 200 mL of toluene was added in one portion. The resulting solution was heated at 80° C. for approximately seventeen hours, after which the solvent was evaporated under reduced pressure, leaving a yellow residue. This residue was dissolved in diethyl ether, and this solution was extracted with 50 mL of hydrochloric acid and 100 mL of water. The organic phase was separated, washed with water, and dried over anhydrous magnesium sulfate. After filtration the solution was evaporated under reduced pressure, leaving an orange solid as a residue. This solid was placed on a silica gel column and eluted with methylene chloride/petroleum ether (50/50). Evaporation of the solvents yielded 6.30 g of 4-methylsalicylaldehyde as a yellow solid, m.p. 51°–53° C. The NMR and IR spectra were consistent with the proposed structure.

Step H: Methyl 2-(formyl-5-methylphenoxy)propionate

A mixture of 6.0 g (0.0441 mole) of 4-methylsalicylaldehyde, 7.31 g (0.0529 mole) of potassium carbonate, and 8.62 g (0.0529 mole) of methyl 2-bromopropionate in 50 mL of 2-butanone was heated at 70° C. for approximately seventeen hours. The mixture was then filtered, and the filtrate was evaporated under reduced pressure, leaving a light yellow oil as a residue. This oil was placed on a silica gel column and eluted first with diethyl ether/petroleum ether (25/75) and then with diethyl ether. After the product-containing fractions were combined and the solvents evaporated under reduced pressure, 8.2 g of methyl 2-(2-formyl-5-methylphenoxy)propionate was recovered as a white solid, m.p. 65°–68° C. The NMR and IR spectra were consistent with the proposed structure.

Step I: Methyl 2-(2-hydroxymethyl-5-methylphenoxy)propionate

To a solution of 7.89 g (0.0355 mole) of methyl 2-(2-formyl-5-methylphenoxy)propionate in 20 mL of methanol, cooled to 5° C., was added a solution of 0.10 g (0.001s mole) of sodium methoxide in 20 mL of methanol. While the temperature was maintained between 0° C. and 5° C., 0.36 g (0.0094 mole) of sodium borohydride was added to the reaction during a period of about 10 minutes. The reaction mixture was allowed to warm to ambient temperature, where it was stirred for two hours. At the end of this period, the reaction mixture was poured into 75 mL of 0.25N hydrochloric acid. This mixture was extracted twice with methylene chloride. The combined extracts were washed with a saturated aqueous solution of sodium chloride, dried over anhydrous magnesium sulfate, and filtered. The filtrate was evaporated under reduced pressure, leaving a colorless oil as a residue. This oil was placed on a silica gel column and eluted first with methylene chloride/ethyl acetate (95/5) and then with the same solvents (90/10). After the product-containing fractions were combined and the solvents evaporated under reduced pressure, 5.76 g of methyl 2-(2-hydroxymethyl-5-methylphenoxy)propionate was isolated as a colorless oil. The NMR and IR spectra were consistent with the proposed structure.

Step J: Methyl 2-(2-chloromethyl-5-methylphenoxy)propionate

A solution of 2.20 g (0.0098 mole) of methyl 2-(2-hydroxymethyl-5-methylphenoxy)propionate in 10 mL of dry methylene chloride was added to a colorless solution of 1.28 g (0.0108 mole) of thionyl chloride and 5 drops of pyridine in 10 mL of dry methylene chloride during a 10 minute period. This mixture was heated at reflux for one hour and then poured into 50 mL of water. The phases were separated, and the aqueous phase was extracted three times with methylene chloride. These extracts were combined with the organic phase, which was then washed three times with a saturated aqueous solution of sodium bicarbonate and once with a saturated aqueous solution of sodium chloride. The organic phase was then dried over anhydrous magnesium sulfate, filtered, and the filtrate was evaporated under reduced pressure, leaving a yellow oil as a residue. This oil was placed on a silica gel column and eluted with methylene chloride. After the product-containing fractions were combined and the solvent evaporated under reduced pressure, 2.06 g of methyl 2-(2-chloromethyl-5-methylphenoxy)propionate was recovered as a colorless oil. The NMR spectrum was consistent with the proposed structure.

Step K: Methyl 2-[2-[4-(4-difluoromethyl-4,5-dihydro-3-methyl-1,2,4-triazol-5(1H)-on-1-yl)-3-fluorophenoxymethyl]-5-methylphenoxy]propionate A mixture of 0.50 g (0.0019 mole) of 1-(2-fluoro-4-hydroxyphenyl)-4-difluoromethyl-4,5-dihydro-3-methyl-1,2,4-triazol-5(1H)-one, 0.39 g (0.0028 mole) of anhydrous potassium carbonate, and 0.92 g (0.0038 mole) of methyl 2-(2-chloromethyl-5-methylphenoxy)propionate in 20 mL of N,N-dimethylformamide was heated at 90° C. for approximately 17 hours. At the end of this period the mixture was poured over ice, and the resulting mixture was extracted with ethyl acetate. The extract was washed with water, dried over anhydrous magnesium sulfate, and filtered. The filtrate was evaporated under reduced pressure, leaving an orange oil as a residue. This oil was placed on a silica gel column and eluted first with methylene chloride and then with methylene chloride/ethyl acetate (97.5/2.5). After the product-containing fractions were combined and the solvents evaporated under reduced pressure, 0.82 g of 2-[2-[4-(4-difluoromethyl-4,5-dihydro-3-methyl-1,2,4-triazol-5(1H)-on-1-yl)-3-fluorophenoxymethyl]-5-methylphenoxy]propionate was recovered as a yellow oil. The NMR and IR spectra were consistent with the proposed structure. NMR: 1.60 (d, 3H, $J_{HH}=8.0$ Hz); 2.30 (s, 3H); 2.44 (s, 3H); 3.76 (s, 3H); 4.84 (q, 1H, $J_{HH}=8.0$ Hz); 5.16 (dd, 2H, $J_{HH}=10.0$ Hz); 6.56 (s, 1H); 6.78–7.32 (m, 6H).

EXAMPLE 2

METHYL 2-[2-[3-FLUORO-4-(3,4,5,6-TETRAHYDRO-1-PHTHALIMIDYL)PHENOXYMETHYL]-5-CHLOROPHENOXY]PROPIONATE (Compound 27)

Step A: Synthesis of 4-amino-3-fluorophenol

To a mixture of 10.0 g (0.0640 mole) of 3-fluoro-4-nitrophenol in 100 mL of acetic acid and 10 mL of water heated to 50° C. was added 10.0 g (0.179 mole) of iron powder in small portions during a 35 minute period. The stirred reaction mixture was heated at 50° C. for an additional three hours, after which it was cooled and filtered. The filtrate was used in Step B without further purification.

Step B: N-(2-fluoro-4-hydroxyphenyl)-3,4,5,6-tetrahydrophthalimide

The filtrate from Step A was mixed with 9.74 g (0.0640 mole) of 3,4,5,6-tetrahydrophthalic anhydride, and the mixture was heated at reflux for approximately 64 hours. At the end of this period, the dark brown solution was poured over ice and extracted in succession with ethyl acetate and diethyl ether. The extracts were combined, washed with water, dried over anhydrous magnesium sulfate, and filtered. The solvents were evaporated under reduced pressure from the filtrate, leaving a dark brown oil as residue. This was placed on a silica gel column and eluted with methylene chloride/ethyl acetate (95/5). After the product-containing fractions were combined and the solvents evaporated under reduced pressure, 14.71 g of N-(2-fluoro-4-hydroxyphenyl)-3,4,5,6-tetrahydrophthalimide was recovered as an orange solid, m.p. 132°–136° C. The NMR spectrum was consistent with the proposed structure.

Step C: 4-Chlorosalicylaldehyde

A 2M solution of ethylmagnesium bromide in tetrahydrofuran (50 ml, 0.10 mole) was placed in a flask, and a solution of 12.85 g (0.10 mole) of 3-chlorophenol in 50 mL of diethyl ether was added slowly with stirring. The addition required two hours, after which the solvents were removed by evaporation under reduced pressure. Toluene (200 ml), 7.50 g (0.25 mole) of paraformaldehyde, and 17.92 g (0.10 mole) of hexamethylphosphoramide were added to the residue, and this mixture was heated at 80° C. for approximately 16 hours. The solvent was evaporated under reduced pressure, leaving a residue. This residue was washed successively with 50 mL of hydrochloric acid and 300 mL of water. Vacuum distillation of the washed residue yielded 11.50 g of 4-chlorosalicylaldehyde, b.p. 112° C. at 9 mm of Hg. This reaction was repeated several times.

Step D: Methyl 2-(5-chloro-2-formylphenoxy)propionate

A mixture of 22.0 g (0.141 mole) of 4-chlorosalicylaldehyde, 30 g (0.22 mole) of anhydrous potassium carbonate, and 30.0 g (0.184 mole) of methyl 2-bromopropionate in 120 mL of N,N-dimethylformamide was heated at 80° C. for approximately 17 hours. At the end of that period, the reaction mixture was poured over ice and extracted successively with diethyl ether and ethyl acetate. The combined extracts were washed with water, dried over anhydrous magnesium sulfate, and filtered. The solvents were then evaporated under reduced pressure, leaving a residue weighing 20 g. This residue was purified by placing it on a silica gel column and eluting with diethyl ether/petroleum ether (25/75). After the product-containing fractions were combined and the solvents evaporated under reduced pressure, 6.23 g of methyl 2-(5-chloro-2-formylphenoxy)propionate was isolated as a yellow liquid. Similarly, other fractions were combined and evaporated, yielding 1.69 g of methyl 2-(3-chloro-2-formylphenoxy)propionate as a yellow liquid. The NMR spectra of both compounds were consistent with proposed structure of each. This reaction was repeated several times.

Step E: Methyl 2-(5-chloro-2-hydroxymethylphenoxy)propionate

To a solution of 0.10 g (0.018 mole) of sodium methoxide in 20 mL of methanol that had been cooled to 5° C. was added a solution of 8.0 g of methyl 2-(5-chloro-2-formylphenoxy)propionate in 20 mL of methanol. While the temperature was maintained between 0° C. and 5° C., to this mixture was added 0.50 g (0.013 mole) of sodium borohydride. This addition required 10 minutes, during which gas was evolved. The yellow solution was allowed to warm up to room temperature, where it was stirred for four hours. At the end of this period the reaction mixture was poured into 100 mL of 0.25N hydrochloric acid. This mixture was extracted with methylene chloride. The extract was washed with a saturated aqueous solution of sodium chloride, dried over anhydrous magnesium sulfate, and filtered. The filtrate was evaporated under reduced pressure, leaving a yellow oil as a residue. This oil was placed on a silica gel column and eluted with methylene chloride/ethyl acetate (95/5). After the product-containing fractions were combined and the solvents evaporated under reduced pressure, 4.42 g of methyl 2-(5-chloro-2-hydroxymethylphenoxy)propionate was isolated as an orange oil, which subsequently solidified, m.p. 51°–52° C.

Step F: Methyl 2-(2-chloromethyl-5-chlorophenoxy)propionate

By the method of Example 1, Step J, 1.0 g (0.0038 mole) of methyl 2-(5-chloro-2-hydroxymethylphenoxy)propionate and 0.5 g (0.0042 mole) of thionyl chloride were reacted in 20 mL of methylene chloride. After purification, 0.88 g of methyl 2-(2-chloromethyl-5-chlorophenoxy)propionate was isolated as a yellow liquid. The NMR spectrum was consistent with the proposed structure.

Step G: Methyl 2-[2-[3-fluoro-4-(3,4,5,6-tetrahydro-1-phthalimidyl)phenoxymethyl]-5-chlorophenoxy]propionate By the method of Example 1, Step K, 0.50 g (0.0019 mole) of N-(2-fluoro-4-hydroxyphenyl)-3,4,5,6-tetrahydrophthalimide, 0.88 g (0.0034 mole) of methyl 2-(2-chloromethyl-5-chlorophenoxy)propionate, and 0.39 g (0.0028 mole) of potassium carbonate were reacted in 20 mL of 2-butanone. After purification, 0.58 g of methyl 2-[2-[3-fluoro-4-(3,4,5,6-tetrahydro-1-phthalimidyl)-phenoxymethyl]-5-chlorophenoxy]propionate was isolated as a yellow solid, m.p. 110°-112° C. The NMR and IR spectra were consistent with the proposed structure. NMR: 1.64 (d, 3H, $J_{HH}$=8 Hz); 1.80 (bs, 4H); 2.40 (bs, 4H); 3,78 (s, 3H); 4.84 (q, 1H, $J_{HH}$=8.0 Hz); 5.14 (s, 2H); 6.78-7.38 (m, 6H).

EXAMPLE 3

METHYL 2-[2-[3-FLUORO-4-[1-(1-METHYLETHYL)-IMIDAZOLIDIN-2,4-DION-3-YL]PHENOXYMETHYL]-5-CHLOROPHENOXY]PROPIONATE (Compound 44)

Step A: 3-Fluoro-4-nitroanisole

A mixture 25.0 g (0.16 mole) of 3-fluoro-4-nitrophenol, 27.6 g (0.20 mole) of potassium carbonate, and 28.4 g (0.20 mole) of methyl iodide in 2-butanone was heated at 70° C. for approximately 17 hours. The reaction mixture was then poured over ice and extracted with diethyl ether. The extract was washed with water, dried over anhydrous magnesium sulfate, and filtered. The filtrate was evaporated under reduced pressure, leaving 24.35 g of 3-fluoro-4-nitroanisole as a solid residue. The NMR spectrum was consistent with the proposed structure. This product was used in Step B without further purification.

Step B: 2-Fluoro-4-methoxyaniline

All of the product from Step A was placed in a Parr hydrogenation apparatus, and 0.35 g of platinum oxide in 200 mL of ethanol was added. This mixture was reacted with hydrogen until the theoretical amount of hydrogen was absorbed. The reaction was stopped, and the reaction mixture was filtered through Celite ® filter aid. The solvent was then evaporated under reduced pressure, leaving 18.5 g of 2-fluoro-4-methoxyaniline as a solid residue.

Step C: 2-Fluoro-4-methoxyphenyl isocyanate

To a solution of 13.75 g (0.0967 mole) of 2-fluoro-4-methoxyaniline in 120 mL of toluene was slowly added over a period of 30 minutes a solution of 19.13 g (0.0967 mole) of trichloromethyl chloroformate in 30 mL of toluene. During the addition the temperature rose to 35° C. The reaction mixture was stirred without external heating for 30 minutes and then heated at reflux for approximately 17 hours. At the end of this time all of the solvent was removed by distillation, leaving 2-fluoro-4-methoxyphenyl isocyanate as a purple liquid, which was used immediately in Step D.

Step D: N-(2-Fluoro-4-methoxyphenyl)-N'-ethoxycarbonylmethylurea

A solution of 2-fluoro-4-methoxyphenyl isocyanate (assumed to weigh 16.2 g (0.0967 mole) from Step C), 13.50 g (0.0967 mole) of glycine ethyl ester hydrochloride in 100 mL of chloroform was placed in a flask, and a solution of 9.28 g (0.0967 mole) of triethylamine in 25 mL of chloroform was added during a 20 minute period. The temperature rose to 38° C. during the addition. Upon completion of addition, the reaction mixture was stirred at ambient temperature for three hours and then poured into a mixture of heptane and water. By filtration, N-2(2-fluoro-4-methoxyphenyl)-N'-ethoxycarbonylmethylurea was isolated from this mixture as a purple solid, m.p. 158°-159° C. The organic phase of the filtrate was separated, dried over anhydrous magnesium sulfate, and filtered. The solvent was evaporated from the filtrate under reduced pressure, leaving a purple solid as residue. This solid was recrystallized from ethyl acetate/petroleum ether. The recrystallized solid was placed on a silica gel column and eluted sequentially with methylene chloride, methylene chloride/ethyl acetate (90/10), and finally methylene chloride/ethyl acetate (75/25). After the product-containing fractions were combined and the solvents evaporated under reduced pressure, additional N-(2-fluoro-4-methoxyphenyl)-N'-ethoxycarbonylmethylurea was isolated as a purple solid, m.p. 158°-159° C. The total yield of N-(2-fluoro-4-methoxyphenyl-N'-ethoxycarbonylmethylurea weighed 17.33 g. The NMR spectra of these solids were consistent with the proposed structure.

Step E: 1-(1-Methylethyl)-3-(2-fluoro-4-methoxyphenyl)imidazolidin-2,4-dione

A solution of 17.02 g (0.0630 mole) of N-(2-fluoro-4-methoxyphenyl)-N'-ethoxycarbonylmethylurea in 50 mL of N,N-dimethylformamide was added dropwise to a suspension of 2.65 g (0.0662 mole) of sodium hydride in 30 mL of N,N-dimethylformamide during a 20 minute period. Gas evolution and a slight rise in temperature occurred during the addition. This mixture was stirred at room temperature for 45 minutes, by which time it had become a homogeneous solution. To this solution was added dropwise, over a period of 15 minutes, a solution of 21.42 g (0.126 mole) of 2-iodopropane in 10 mL of N,N-dimethylformamide. The temperature rose to 38° C. during the addition period. This reaction mixture was stirred for approximately 65 hours, then poured over ice and extracted with diethyl ether. The extract was washed twice with water, dried over anhydrous magnesium sulfate, and filtered. The filtrate was evaporated under reduced pressure, leaving an orange oil as a residue. This oil was placed on a silica gel column and eluted sequentially with 97.5/2.5 and 95/5 mixtures of methylene chloride and ethyl acetate. After the product-containing fractions were combined and the solvents evaporated under reduced pressure, 5.85 g of 1-(1-methylethyl-3-(2-fluoro-4-methoxyphenyl-)imidazolidin-2,4-dione was isolated as an orange solid, m.p. 88°-90° C.

Step F: 1-(1-methylethyl)-3-(2-fluoro-4-hydroxyphenyl)imidazolidin-2,4-dione

A 1M methylene chloride solution of boron tribromide (41.6 ml, 0.0416 mole) was cooled to −20° C. While this temperature was maintained, a solution of 5.55 g (0.0208 mole) of 1-(1-methylethyl)-3-(2-fluoro-4-methoxyphenyl)imidazolidin-2,4-dione in 25 mL of methylene chloride was added to the reaction during an eight minute period. The reaction mixture was allowed to warm to room temperature, where it was stirred for approximately 17 hours. At the end of this time the reaction was poured over ice, and the resulting two-phase mixture was filtered. The organic phase was separated, dried over anhydrous magnesium sulfate, and filtered. The filtrate was evaporated under reduced pressure, leaving a black solid as a residue. This solid was recrystallized from ethyl acetate/petroleum ether, to yield 3.25 g of 1-(1-methylethyl)-3-(2-fluoro-4-hydroxyphenyl)imidazolidin-2,4-dione as a tan solid, m.p. 190°-192° C. The NMR and IR spectra were consistent with the proposed structure.

Step G: Methyl 2-[2-[3-fluoro-4-[1-(1-methylethyl)imidazolidin-2,4-dion-3-yl]phenoxymethyl]-5-chlorophenoxy]propionate By the method of Example 1, Step K, 0.60 g (0.0024 mole) of 1-(1-methylethyl)-3-(2-fluoro-4-hydroxyphenyl)imidazolidin-2,4-dione, 1.24 g (0.0048 mole) of methyl 2-(2-chloromethyl-5-chlorophenoxy)propionate (Example 2, Step F), and 0.5 g (0.0036 mole) of potassium carbonate were reacted in 25 mL of 2-butanone. After purification, 1.04 g of methyl 2-[2-[3-fluoro-4-[1-(1-methylethyl)imidazolidin-2,4-dion-3-yl]phenoxymethyl]-5-chlorophenoxy]propionate was isolated as a yellow oil. The NMR and IR spectra were consistent with the proposed structure. NMR: 1.24 (d, 6H, $J_{HH}=8$ Hz); 1.64 (d, 3H, $J_{HH}=8$ Hz); 3.68 (s, 3H); 3.96 (s, 1H); 4.44 (septet, 1H, $J_{HH}=8.0$ Hz); 5.04 (q, 1H, $J_{HH}=8.0$ Hz); 5.24 (s, 2H); 6.80–7.34 (m, 5H).

EXAMPLE 4

METHYL 2-[2-[4-[1,4-DIHYDRO-4-(3-FLUOROPROPYL)-5H-TETRAZOL-5-ON-1-YL]-3-FLUOROPHENOXYMETHYL]-5-METHYLPHENOXY]PROPIONATE (Compound 64)

Step A: 4-Fluorophenylmethyl 3-fluoro-4-nitrophenyl ether

A stirred mixture of 10.0 g (0.063 mole) of 3-fluoro-4-nitrophenol, 17.0 g (0.090 mole) of 4-fluorophenylmethyl chloride, and 12.42 g (0.090 mole) of anhydrous potassium carbonate in 80 mL of methyl ethyl ketone was heated at 70° C. for approximately 17 hours. The reaction mixture was then cooled and filtered and the filtrate evaporated under reduced pressure, leaving 13.10 g of 4-fluorophenylmethyl 3-fluoro-4-nitrophenyl ether as a solid; m.p. 90°–91° C.

Step B: 4-Fluorophenylmethyl 4-amino-3-fluorophenyl ether

A solution of 11.0 g (0.041 mole) of 4-fluorophenylmethyl 3-fluoro-4-nitrophenyl ether in 100 mL of glacial acetic acid and 10 mL of water was heated to 50° C. To this hot solution was added 1.0 g (0.18 mole) of powdered iron. The reaction mixture was allowed to cool to ambient temperature, where it stirred for an additional hour. The reaction mixture was filtered through a bed of Celite ® filter aid, and the Celite bed was washed in succession with ethyl acetate and 200 mL of water. The washes and the filtrate were combined, and the organic phase was separated. The organic phase was dried with anhydrous magnesium sulfate, filtered, and the solvent was evaporated under reduced pressure, leaving a dark oil as a residue. This oil was placed on a silica gel column and eluted with methylene chloride. The product-containing fractions were combined and the solvent evaporated under reduced pressure, leaving 6.8 g of 4-fluorophenylmethyl 4-amino-3-fluorophenyl ether as a solid, m.p. 42°–43° C.

Step C: 4-(4-Fluorophenylmethoxy)-2-fluorophenyl isocyanate

To a solution of 6.50 g (0.0276 mole) of 4-fluorophenylmethyl 4-amino-3-fluorophenyl ether in toluene, stirring at room temperature, was slowly added 3.95 g (0.020 mole) of trichloromethyl chloroformate. During the addition a thick precipitate formed. Upon completion of addition, the reaction mixture was stirred for one hour at room temperature and then at reflux for approximately seventeen hours. The toluene was removed by distillation, leaving 7.10 g of 4-(4-fluorophenylmethoxy)-2-fluorophenyl isocyanate.

Step D: 1-[4-(4-Fluorophenylmethoxy)-2-fluorophenyl]-1,4-dihydro-5H-tetrazol-5-one A mixture of 7.10 g (0.027 mole) of 4-(4-fluorophenylmethoxy)-2-fluorophenyl isocyanate and 7.0 g (0.060 mole) of trimethylsilyl azide was heated at reflux for approximately seventeen hours. The solution was then allowed to cool to room temperature before being poured over ice. A solid formed and was recovered by filtration. The solid was dried, leaving 8.08 g of 1-[4-(4-fluorophenylmethoxy)-2-fluorophenyl]-1,4-dihydro-5H-tetrazol-5-one, m.p. 171°–172° C.

Step E: 1-[4-(4-Fluorophenylmethoxy)-2-fluorophenyl]-1,4-dihydro-4-(3-fluoropropyl)-5H-tetrazol-5-one A mixture of 7.0 g (0.023 mole) of 1-[4-(4-fluorophenylmethoxy)-2-fluorophenyl]-1,4-dihydro-5H-tetrazol-5-one, 4.23 g (0.030 mole) of 1-bromo-3-fluoropropane, and 4.14 g (0.030 mole) of anhydrous potassium carbonate in 60 mL of N,N-dimethylformamide was heated at 70° C. for approximately seventeen hours. The mixture was allowed to cool to room temperature before being poured over ice. The solid that formed was removed by filtration and dried. This solid was then placed on a silica gel column and eluted with with methylene chloride. The product-containing fractions were combined and the solvents evaporated under reduced pressure, leaving 6.35 g of 1-[4-(4-fluorophenylmethoxy)-2-fluorophenyl]-1,4-dihydro-4-(3-fluoropropyl)-5H-tetrazol-5-one, m.p. 86°–88° C.

Step F: 1-(2-Fluoro-4-hydroxyphenyl)-1,4-dihydro-4-(3-fluoropropyl)-5H-tetrazol-5-one -To a solution of 5.60 g (0.0153 mole) of 1-[4-(4-fluorophenylmethoxy)-2-fluorophenyl]-1,4-dihydro-4-(3-fluoropropyl)-5H-tetrazol-5-one in 60 mL of glacial acetic acid was added 5 mL of 49% hydrobromic acid. This mixture was heated at reflux for 90 minutes, after which it was cooled to room temperature. The reaction mixture was then poured over ice, and the resulting aqueous solution was extracted with diethyl ether. The combined extract was dried over magnesium sulfate, filtered, and the solvent was evaporated under reduced pressure, leaving 4.35 g of 1-(2-fluoro-4-hydroxyphenyl)-1,4-dihydro-4-(3-fluoropropyl)-5H-tetrazol-5-one as a residue.

Step G: Methyl 2-[2-[4-[1,4-dihydro-4-(3-fluoropropyl)-5H-tetrazol-5-on-1-yl]-3-fluorophenoxymethyl]-5-methylphenoxy]propionate By the method Example 1, Step K, 0.85 g (0.0033 mole) of 1-(2-fluoro-4-hydroxyphenyl)-1,4-dihydro-4-(3-fluoropropyl)-5H-tetrazol-5-one and 1.21 g (0.0050 mole) of methyl 2-(2-chloromethyl-5-methylphenoxy)propionate (Example 1, Step J) were reacted in the presence of 0.70 g (0.0050 mole) of anhydrous potassium carbonate in 60 mL of N,N-dimethylformamide, yielding 0.42 g of methyl 2-[2-[4-[1,4-dihydro-4-(3-fluoropropyl)-5H-tetrazol-5-on-1-yl]-3-fluorophenoxymethyl]-5-methylphenoxy]propionate as an oil. The NMR spectrum was consistent with the proposed structure. NMR: 1.64 (d, 3H, $J_{HH}=8$ Hz); 2.2–2.4 (m, 2H); 2,32 (s, 3H); 3.72 (s, 3H); 4.18 (t, 2H, $J_{HH}=8$ Hz); 4.50–4.64 (dt, 2H, $J_{HH}=8$ Hz, $J_{HF}=45$ Hz); 4.84 (q, 1H, $J_{HH}=8$ Hz), 5.20 (q, 2H, $J_{HH}=8$ Hz); 6.58–7.40 (m, 6H).

EXAMPLE 5

METHYL 2-[2-[4-(3-CHLORO-4,5,6,7-TETRAHYDROINDAZOL-2-YL)-3-FLUOROPHENOXYMETHYL]-5-CHLOROPHENOXY]PROPIONATE (Compound 66)

Step A: 2-Fluoro-4-methoxyphenylhydrazine

With vigorous stirring, 9.15 g (0.065 mole) of 2-fluoro-4-methoxyaniline (Example 3, Step B) was added to 60 mL of concentrated hydrochloric acid that had been cooled to −10° C. A solution of 4.83 g (0.070 mole) of sodium nitrite in 30 mL of water was slowly added dropwise, while the temperature was kept at or below −10° C. Upon completion of addition, the reaction mixture was stirred at −10° C. for one hour, after which 33.85 (0.150 mole) of tin(II) chloride dihydrate in 50 mL of concentrated hydrochloric acid Was added slowly, dropwise, while the temperature was kept below −5° C. After the reaction mixture had stirred for one hour as it warmed to ambient temperature, the crude product was filtered from the mixture and dissolved in 250 mL of water. This solution was made basic with 4N sodium hydroxide and extracted with methylene chloride. The combined extracts were dried over anhydrous sodium sulfate and filtered. The filtrate was placed on a silica gel column and eluted with methylene chloride to remove colored impurities and then with ethyl acetate to obtain the desired product. The solvent was evaporated under reduced pressure to yield 6.30 g of 2-fluoro-4-methoxyphenylhydrazine. The NMR spectrum was consistent with the proposed structure.

Step B: 2-(2-Fluoro-4-methoxyphenyl)-4,5,6,7-tetrahydro-1H-indazol-3-one

To a solution of 6.28 g (0.040 mole) of 2-fluoro-4-methoxyphenylhydrazine in 200 mL of toluene was added with stirring 6.82 g (0.040 mole) of ethyl 2-cyclohexanonecarboxylate. This mixture was heated at reflux under a nitrogen atmosphere while water was removed with a Dean-Stark trap. When all water had been removed, the reaction mixture was cooled, and the solvent was evaporated under reduced pressure, leaving a residue which was then dissolved in acetic acid. This solution was heated at reflux for approximately sixteen hours, after which the solvent was evaporated under reduced pressure, leaving a residue. This residue was dissolved in toluene, which was also evaporated under reduced pressure. The residue was dissolved in ethyl acetate and placed on a silica gel column and eluted with ethyl acetate. An attempt to crystallize the product by dissolving it in diethyl ether after the ethyl acetate had been evaporated was unsuccessful. After the solvent had been evaporated from this product, it was again heated at reflux in acetic acid for 24 hours and allowed to cool to room temperature, where the solution stirred for an additional 48 hours. The solvent was evaporated under reduced pressure, leaving a residue weighing 4.32 g. Two additional fractions weighing 0.80 g and 2.75 g had been recovered by extracting the reaction mixture before the solvent was evaporated. The NMR spectrum of the residue showed it to be a mixture of 2-(2-fluoro-4-methoxyphenyl)-4,5,6,7-tetrahydro-1H-indazol-3-one and the 2-fluoro-4-methoxyphenylhydrazone of 2-cyclohexanonecarboxylic acid.

Step C: 3-Chloro-2-(2-fluoro-4-methoxyphenyl)-4,5,6,7-tetrahydro-1H-indazole

The 4.32 g residue from Step B was mixed at ambient temperature with 5.37 g (0.035 mole) of phosphorus oxychloride until complete dissolution occurred. At this point the reaction mixture was heated at reflux under nitrogen for one hour. The phosphorus oxychloride was evaporated from the reaction mixture under reduced pressure, leaving a residue weighing 1.50 g. This residue, together with a similar residue weighing 0.30 g from an earlier experiment, was then was placed on a silica gel column and eluted with hexane/ethyl acetate (4:1). After the product-containing fractions were combined and the solvents evaporated under reduced pressure, 0.50 g of 3-chloro-2-(2-fluoro-4-methoxyphenyl)-4,5,6,7-tetrahydroindazole was isolated. The NMR was consistent with the proposed structure.

Step D: 3-Chloro-2-(2-fluoro-4-hydroxyphenyl)-4,5,6,7-tetrahydroindazole

A 1N solution of boron tribromide in methylene chloride (18.0 mL, 0.018 mole) was diluted with 17 mL of methylene chloride and was then cooled to below −10° C. under a nitrogen atmosphere. A solution of 3-chloro-2-(2-fluoro-4-methoxyphenyl)-4,5,6,7-tetrahydroindazole in 25 mL of methylene chloride was added dropwise at a rate to maintain the temperature below −10° C. Upon completion of addition, the reaction mixture was allowed to warm to ambient temperature at which it stirred for sixteen hours. The mixture was then poured into ice-water, and the resulting mixture was stirred for 30 minutes. This mixture was filtered, and the filtrate was passed through a short column of silica gel. The organic phase was separated, dried with anhydrous sodium sulfate, and filtered. The solvent was evaporated from the filtrate under reduced pressure, leaving 0.60 g of 3-chloro-2-(2-fluoro-4-hydroxyphenyl)-4,5,6,7-tetrahydroindazole as a nearly white solid, m.p. 214°−216° C. The NMR and IR spectra were consistent with the proposed structure.

Step E: Methyl 2-[2-[4-(3-chloro-4,5,6,7-tetrahydroindazol-2-yl)-3-fluorophenoxymethyl]-5-chlorophenoxy]propionate By the method of Example 1, Step K, 0.49 g (0.0016 mole) of 3-chloro-2-(2-fluoro-4-hydroxyphenyl)-4,5,6,7-tetrahydroindazole and 0.52 g (0.002 mole) of methyl 2-(2-chloromethyl-5-chlorophenoxy)propionate (Example 2, Step F) were reacted in the presence of 0.41 g (0.003 mole) of anhydrous potassium carbonate in 30 mL of N,N-dimethylformamide, yielding 0.64 g of methyl 2-[2-[4-(3-chloro-4,5,6,7-tetrahydroindazol-2-yl)-3-fluorophenoxymethyl]-5-chlorophenoxy]propionate as a syrup. The NMR and IR spectra were consistent with the proposed structure. NMR: 1.64 (d, 3H, $J_{HH}$=8.0 Hz); 1.82 (m, 4H); 2.50 (t, 2H, $J_{HH}$=4.0 Hz); 2.68 (t, 2H, $J_{HH}$=4.0 Hz); 3.76 (s, 3H); 4.82 (q, 1H, $J_{HH}$=8 Hz); 5.18 (s, 2H,); 6.78−7.40 (m, 6H).

EXAMPLE 6

METHYL 2-[2-[4-(4-METHYL-1,2,4-TRIAZINE-3,5-DION-2-YL)-3-FLUOROPHENOXYMETHYL]-5-METHYLPHENOXY]PROPIONATE (Compound 70)

Step A: 4-Isopropoxy-2-fluoronitrobenzene

By the method of Example 3, Step A, 23.15 g (0.147 mole) of 3-fluoro-4-nitrophenol and 29.92 g (0.175 mole) of 2-iodopropane were reacted in the presence of 20.73 g (0.150 mole) of anhydrous potassium carbonate in 450 mL of acetone, yielding 28.0 g of 4-isopropoxy-2-fluoronitrobenzene as an oil. The NMR was consistent with the proposed structure.

Step B: 4-Isopropoxy-2-fluoroaniline

A stirred flask containing 350 mL of acetic acid was heated to 80°−85° C. under a nitrogen atmosphere. To this flask was added 39.10 g (0.700 mole) of powdered iron, and this mixture was stirred for one hour. A solution of 4-isopropoxy-2-fluoronitrobenzene in 250 mL was added to the mixture dropwise. Upon completion of addition, the reaction mixture was heated at 80°−85° C. for one hour. After being cooled below 40° C., the mixture was filtered, and the solvent was evaporated under reduced pressure, leaving a residue. This residue was dissolved in a mixture of water and diethyl ether. The organic layer was separated and was washed in succession with saturated aqueous solutions of sodium bicarbonate and sodium chloride. It was then dried over anhydrous magnesium sulfate, filtered through a short column of silica gel, and the solvent was evaporated under reduced pressure, leaving an impure residue which contained significant amounts of acetamide in addition to the desired product. This residue was suspended in 500 mL of 2N hydrochloric acid for one hour. The hydrochloric acid mixture was then extracted with diethyl ether, and the two phases were separated. Aqueous sodium hydroxide solution was added to the aqueous hydrochloride solution until it was basic. This basic solution was extracted with diethyl ether, and the extract was dried over anhydrous magnesium sulfate and filtered. After evaporation of the solvent under reduced pressure, the residue was recrystallized from diethyl ether/petroleum ether to yield 16.90 g of 4-isopropoxy-2-fluoroaniline as an oil which darkened on standing. The NMR spectrum was consistent with the proposed structure.

Step C: Malonyldiurethane

With a mortar and pestle 10.40 g (0.100 mole) of malonic acid and 18.00 g (0.210 mole) of ethyl carbamate were ground to a fine powder. This powder was placed in a flask, and 16.0 mL (0.167 mole) of phosphorus oxychloride was added. This mixture was heated at 80° C. until the evolution of gas ceased. After this reaction mixture had cooled to ambient temperature, 210 mL of water was added. When the stiff glassy mixture became fluid, it was extracted with ethyl acetate. The combined extracts were washed in succession with saturated aqueous solutions of sodium bicarbonate and sodium chloride and were then dried over anhydrous magnesium sulfate and filtered. The solution was filtered through a short column of silica gel, which was eluted with ethyl acetate. The solvent was then evaporated under reduced pressure, leaving a crystalline mass of malonyldiurethane weighing 10.62 g. The NMR spectrum was consistent with the proposed structure.

Step D: 2-(4-Isopropoxy-2-fluorophenyl)hydrazonomalonyldiurethane

A mixture of 5.92 g (0.035 mole) of 4-isopropoxy-2-fluoroaniline, 10.60 g (0.043 mole) of malonyldiurethane, and 41.02 g (0.500 mole) of sodium acetate was suspended in 1000 mL of water with vigorous stirring. To this suspension was added 25 mL of 12N hydrochloric acid. The reaction mixture was cooled to 10° C., and, while this temperature was maintained, a solution of 2.42 g (0.035 mole) of sodium nitrite in 25 mL of water was slowly added. The reaction mixture was allowed to warm slowly to room temperature where it was stirred under a nitrogen atmosphere for approximately 16 hours. During this period a yellow solid formed and precipitated out. The mixture was filtered, and the yellow solid was washed in succession with water and diethyl ether. After being dried, 9.20 g of 2-(4-isopropoxy-2-fluorophenyl)hydrazonomalonyldiurethane was isolated as a yellow solid. The NMR and IR spectra were consistent with the proposed structure.

Step E: 2-(4-Isopropoxy-2-fluorophenyl)-1,2,4-triazine-3,5-dion-6-carboxylic acid To a stirred solution of 8.94 g (0.021 mole) of 2-(4-isopropoxy-2-fluorophenyl)hydrazonomalonyldiurethane in 125 mL of ethanol and 125 mL of tetrahydrofuran was added 75 mL (0.134 mole) of 10% aqueous potassium hydroxide, initially forming a precipitate, which subsequently dissolved. After this mixture was stirred for 30 minutes at ambient temperature, 30 mL of 11.7N hydrochloric acid was added carefully with stirring. The tetrahydrofuran was evaporated under reduced pressure, and the residue was then extracted with ethyl acetate. The combined extracts were treated with decolorizing charcoal, dried over anhydrous magnesium sulfate, and filtered through a short column of silica gel, which was eluted with ethyl acetate. The solvent was evaporated from the filtrate, yielding 4.70 g of 2-(4-isopropoxy-2-fluorophenyl)-1,2,4-triazine-3,5-dion-6-carboxylic acid as an amorphous foam. The NMR spectrum was consistent with the proposed structure.

Step F: 2-(4-Isopropoxy-2-fluorophenyl)-1,2,4-triazine-3,5-dione

A solution of 4.70 g 0.0152 mole) of 2-(4-isopropoxy-2-fluorophenyl)-1,2,4-triazine-3,5-dion-6-carboxylic acid in 5 mL of mercaptoacetic acid was heated at 140°–145° C. for two hours under a nitrogen atmosphere. After this mixture had cooled, it was poured into 250 mL of a saturated aqueous solution of sodium bicarbonate with vigorous stirring. An equal volume of ethyl acetate was added to this mixture, and the resulting layers were separated. The organic layer was washed twice with 150 mL of a saturated aqueous solution of sodium bicarbonate and once with 150 mL of a saturated aqueous solution of sodium chloride. The organic solution was then dried over anhydrous magnesium sulfate and filtered. The solvent was evaporated under reduced pressure, leaving a syrup which slowly crystallized to a yellow-orange solid upon standing. This solid was recrystallized from ethyl acetate/petroleum ether (1:1), yielding 0.60 g of 2-(4-isopropoxy-2-fluorophenyl)-1,2,4-triazine-3,5-dione as a yellow solid. The NMR was consistent with the proposed structure. This reaction was repeated to obtain additional material for subsequent reactions.

Step G: 2-(4-Isopropoxy-2-fluorophenyl)-4-methyl-1,2,4-triazine-3,5-dione

A solution of 3.25 g (0.0123 mole) of 2-(4-isopropoxy-2-fluorophenyl)-1,2,4-triazine-3,5-dione in 30 mL of N,N-dimethylformamide was added to a suspension of 0.50 g (0.0125 mole) of sodium hydride in 30 mL of N,N-dimethylformamide at ambient temperature. When gas evolution had ceased, 3.55 g (0.025 mole) of iodomethane was added in one portion. This mixture was stirred for one hour without heating and was then poured into 300 mL of dilute hydrochloric acid. The resulting mixture was extracted several times with diethyl ether, and the extracts were combined. The ether extract was washed in succession with water and a saturated aqueous solution of sodium chloride. It was then dried over anhydrous magnesium sulfate and filtered through a short column of silica gel. The solvent was evaporated under reduced pressure, leaving 2.80 g of 2-(4-isopropoxy-2-fluorophenyl)-4-methyl-1,2,4-triazine-3,5-dione as a syrup. The NMR was consistent with the proposed structure.

Step H: 2-(4-Hydroxy-2-fluorophenyl)-4-methyl-1,2,4-triazine-3,5,-dione

Concentrated sulfuric acid (5 mL) that had been cooled to 0°–5° C. was mixed with 2.80 g (0.010 mole) of 2-(4-isopropoxy-2-fluorophenyl)-4-methyl-1,2,4-triazine-3,5-dione that had been cooled to 0° C. The mixture was maintained at 0° C. for ten minutes, during which time it became homogeneous. The mixture was then poured into ice-water, and the resulting mixture was extracted with ethyl acetate. The extract was washed in succession with a saturated aqueous solution of sodium bicarbonate and a saturated aqueous solution of sodium chloride. The extract was dried over anhydrous magnesium sulfate and filtered. The solvent was evaporated from the filtrate under reduced pressure, leaving a residue. This residue was placed on a column of silica gel and eluted with ethyl acetate/hexane (1:1). After the product-containing fractions were combined and the solvents evaporated under reduced pressure, 1.38 g of 2-(4-hydroxy-2-fluorophenyl)-4-methyl-1,2,4-triazine-3,5-dione was recovered as a stiff syrup. The NMR was consistent with the proposed structure.

Step I: Methyl 2-[2-[4-(4-methyl-1,2,4-triazine-3,5-dion-2-yl)-3-fluorophenoxymethyl]-5-methylphenoxy]propionate By the method of Example 1, Step K, 0.47 g (0.002 mole) of 2-(4-hydroxy-2-fluorophenyl)-4-methyl-1,2,4-triazine-3,5-dione and 0.73 g (0.003 mole) of methyl 2-(2-chloromethyl-5-methylphenoxy)propionate were reacted in the presence of 0.41 g (0.003 mole) of anhydrous potassium carbonate in 30 mL of N,N-dimethylformamide, yielding 0.70 g of methyl 2-[2-[4-(4-methyl-1,2,4-triazine-3,5-dion-2-yl)-3-fluorophenoxymethyl]-5-methylphenoxy]propionate as a syrup. The IR and NMR spectra were consistent with the proposed structure. NMR: 1.60 (d, 3H, $J_{HH}=8.0$ Hz); 2.30 (s, 3H); 3.40 (s, 3H); 3.78 (s, 3H); 4.84 (q, 1H, $J_{HH}=8.0$ Hz); 5.18 (dd, 2H, $J_{HH}=10$ Hz); 6.58 (s, 1H); 6.8–7.3 (m, 5H); 7.54 (s, 1H).

EXAMPLE 7

METHYL 2-[2-[4-(4-DIFLUOROMETHYL-4,5-DIHYDRO-3-METHYL-1,2,4-TRIAZOL-5(1H)-ON-1-YL)-3-FLUOROPHENYLTHIOMETHYL]-5-CHLOROPHENOXY]PROPIONATE (Compound 72)

Step A 4-(4-Difluoromethyl-4,5-dihydro-3-methyl-1,2,4-triazol-5(1H)-on-1-yl)-3-fluorophenylsulfonyl chloride A mixture of 2.02 g (0.0078 mole) of 1-(2-fluoro-4-aminophenyl)-4-difluoromethyl-4,5-dihydro-3-methyl-1,2,4,-triazol-5(1H)-one (Example 1, Step E) in 20 mL of hydrochloric acid was cooled to 0° C., and 0.55 g (0.0084 mole) of sodium nitrite in 5 mL of water was added slowly while the temperature was held at 0°–5° C. The yellow solution was then stirred at room temperature for two hours. Meanwhile a solution of 1.08 g (0.0080 mole) of copper(II) chloride in 5 mL of water and 20 mL of acetic was prepared, and sulfur dioxide was bubbled through this solution until it was saturated, a period of ten minutes. After having been stirred for two hours, the yellow solution was added slowly to the solution saturated with sulfur dioxide. The mixture turned green, and a yellow precipitate formed. During the addition, the temperature rose to 32° C. The reaction mixture was stirred for an hour at room temperature and then poured over ice. The pale yellow solid that formed was isolated by filtration, yielding 1,86 g of 4-(4-difluoromethyl-4,5-dihydro-3-methyl-1,2,4-triazol-5(1H)-on-1-yl)-3-fluorophenylsulfonyl chloride. The NMR spectrum was consistent with the proposed structure. This reaction was repeated to obtain additional product for subsequent reactions.

Step B 4-(4-Difluoromethyl-4,5-dihydro-3-methyl-1,2,4-triazol-5(1H)-on-1-yl)-3-fluorothiophenol Gaseous hydrogen chloride was bubbled into a mixture of 3.29 g (0.0146 mole) of tin(II) chloride in 40 mL of acetic acid for about five minutes, causing it to become a clear solution. This solution was then heated to 85° C., and a hot solution of 1.66 g (0.00485 mole) of 4-(4-difluoromethyl-4,5-dihydro-3-methyl-1,2,4-triazol-5(1H)-on-1-yl)-3-fluorophenylsulfonyl chloride was added to the first solution. This reaction mixture was heated at 85° C. for 45 minutes. After cooling to room temperature, the resulting yellow solution was poured into 120 mL of hydrochloric acid. To this mixture was added 100 mL of a saturated aqueous solution of sodium chloride, and the resulting mixture was extracted with ethyl acetate, but the layers did not separate. The addition of a saturated aqueous solution of sodium chloride did effect a partial separation. The aqueous layer was extracted two more times with ethyl acetate, and all extracts were combined. After evaporation of the solvent under reduced pressure, the residue retained an odor of hydrochloric acid. Water was added to the residue, and this mixture was extracted three times with ethyl acetate. The combined extracts were washed with water, dried over anhydrous magnesium sulfate, and filtered. Following evaporation of the solvent under reduced pressure, the yellow residue that remained was dried under vacuum. This dried residue was placed on a column of silica gel and eluted with methylene chloride/ethyl acetate (2:1). After being dried under vacuum for several hours, 0.81 g of 4-(4-difluoromethyl-4,5-dihydro-3-methyl-1,2,4-triazol-5(1H)-on-1-yl)-3-fluorothiophenol was isolated as a yellow syrup. The NMR spectrum was consistent with the proposed structure. This reaction was repeated to obtain additional product for subsequent reactions.

Step C Methyl 2-[2-[4-(4-difluoromethyl-4,5-dihydro-3-methyl-1,2,4-triazol-5(1H)-on-1-yl)-3-fluorophenylthiomethyl]-5-chlorophenoxy]propionate By the method of Example 1, Step K, 1.35 g (0.0049 mole) of 4-(4-difluoromethyl-4,5-dihydro-3-methyl-1,2,4-triazol-5(1H)-on-1-yl)-3-fluorothiophenol and 3.0 g (0.011 mole) of methyl 2-(2-chloromethyl-5-chlorophenoxy)propionate (Example 2, Step F) were reacted in the presence of 1.02 g (0.0074 mole) of anhydrous potassium carbonate in 75 mL of N,N-dimethylformamide, yielding 0.54 g of methyl 2-[2-[4-(4-difluoromethyl-4,5-dihydro-3-methyl-1,2,4-triazol-5(1H)-on-1-yl)-3-fluorophenylthiomethyl]-5-chlorophenoxy]propionate as a yellow syrup. The NMR spectrum was consistent with the proposed structure. NMR: 1.65 (d, 3H, $J_{HH}=8.0$ Hz); 2.44 (s, 3H); 3.78 (s, 3H); 4.20 (dd, 2H, $J_{HH}=13.0$ Hz); 4.78 (q, 1H, $J_{HH}=8.0$ Hz); 6.70–7.38 (m, 7H).

EXAMPLE 8

METHYL [2-[4-(4-DIFLUOROMETHYL-4,5-DIHYDRO-3-METHYL-1,2,4-TRIAZOL-5(1H)-ON-1-YL)-3-FLUOROPHENOXYMETHYL]-5-METHYLPHENOXY]ACETATE (Compound 75)

Step A Methyl (2-formyl-5-methylphenoxy)acetate

By the method of Example 1, Step H, 8,27 g (0.060 mole) of 4-methylsalicylaldehyde (Example 1, Step G) and 11.15 g (0.073 mole) of methyl bromoacetate were reacted in the presence of 10.1 g (0.073 mole) of anhydrous potassium carbonate in 150 mL of acetone, yielding 11.47 g of methyl (2-formyl-5-methylphenoxy)acetate as a white solid, m. p. 63°-64° C. The NMR was consistent with the proposed structure.

Step B Methyl (2-hydroxymethyl-5-methylphenoxy)acetate

By the method of Example 1, Step I, 11.27 g (0.054 mole) of methyl (2-formyl-5-methylphenoxy)acetate was reacted with 0.54 g (0.014 mole) of sodium borohydride and 0.10 g (0.0018 mole) of sodium methoxide in 30 mL of methanol, yielding 9.41 g of methyl (2-hydroxymethyl-5-methylphenoxy)acetate as a yellow oil. The NMR spectrum was consistent with the proposed structure.

Step C Methyl (2-chloromethyl-5-methylphenoxy)acetate

By the method of Example 1, Step J, 9.21 g (0.044 mole) of methyl (2-hydroxymethyl-5-methylphenoxy)acetate was reacted with 7.40 g (0.062 mole) of thionyl chloride and 5 drops of pyridine in 50 mL of methylene chloride, yielding 5.57 g of methyl (2-chloromethyl-5-methylphenoxy)acetate as an orange liquid.

Step D Methyl [2-[4-(4-difluoromethyl-4,5-dihydro-3-methyl-1,2,4-triazol-5(1H)-on-1-yl)-3-fluorophenoxymethyl]-5-methylphenoxy]acetate By the method of Example 1, Step K, 2.0 g (0.0077 mole) of 1-(2-fluoro-4-hydroxyphenyl)-4-difluoromethyl-4,5-dihydro-3-methyl-1,2,4-triazol-5(1H)-one (Example 1, Step F) and 3.53 g (0.0151 mole) of methyl (2-chloromethyl-5-methylphenoxy)acetate were reacted in the presence of 1.60 g (0.0116 mole) of anhydrous potassium carbonate in 40 mL of N,N-dimethylformamide, yielding 2.75 g of methyl [2-[4-(4-difluoromethyl-4,5-dihydro-3-methyl-1,2,4-triazol-5(1H)-on-1-yl)-3-fluorophenoxymethyl]-5-methylphenoxy]acetate. The NMR spectrum was consistent with the proposed structure. NMR: 2.30 (s, 3H); 2.44 (s, 3H); 3.78 (s, 3H); 4.70 (s, 2H); 5.18 (s, 2H); 6.60–7.36 (m, 7H).

EXAMPLE 9

2-[3-[4-(4-DIFLUOROMETHYL-4,5-DIHYDRO-3-METHYL-1,2,4-TRIAZOL-5(1H)-ON-1-YL)-3-FLUOROPHENOXYMETHYL]PHENOXY]PROPIONATE (Compound 80)

Step A Methyl 2-(3-formylphenoxy)propionate

By the method of Example 1, Step H, 10.0 g (0.0819 mole) of 3-hydroxybenzaldehyde and 16.0 g (0.0982 mole) of methyl 2-bromopropionate were reacted in the presence of 13.6 g (0.0983 mole) of anhydrous potassium carbonate in 50 mL of N,N-dimethylformamide, yielding 16.1 g of methyl 2-(3-formylphenoxy)propionate as an orange liquid. The NMR and IR spectra were consistent with the proposed structure.

Step B Methyl 2-(3-hydroxymethylphenoxy)propionate

By the method of Example 1, Step I, 15.7 g (0.0761 mole) of methyl 2-(3-formylphenoxy)propionate, 0.76 g (0.020 mole) of sodium borohydride, and 0.10 g (0.0018 mole) of sodium methoxide were reacted in 40 mL of methanol, yielding 15.6 g of methyl 2-(3-hydroxymethylphenoxy)propionate as a yellow liquid. The NMR and IR spectra were consistent with the proposed structure.

Step C Methyl 2-(3-chloromethylphenoxy)propionate

By the method of Example 1, Step J, 1.98 g (0.0095 mole) of methyl 2-(3-hydroxymethylphenoxy)propionate and 1.24 g (0.0105 mole) of thionyl chloride were reacted in the presence of five drops of pyridine in 40 mL of methylene chloride, yielding 1.93 g of methyl 2-(3-chloromethylphenoxy)propionate as a yellow liquid. The NMR and IR spectra were consistent With the proposed structure.

Step D Methyl 2-[3-[4-(4-difluoromethyl-4,5-dihydro-3-methyl-1,2,4-triazol-5(1H)-on-1-yl)-3-fluorophenoxymethyl]phenoxy]propionate By the method of Example 1, Step K, 1.0 g (0.0038 mole) of 1-(2-fluoro-4-hydroxyphenyl)-4-difluoromethyl-4,5-dihydro-3-methyl-1,2,4-triazol-5(1H)-one (Example 1, Step F) and 1.72 g (0.0076 mole) of methyl 2-(3-chloromethylphenoxy)propionate were reacted in the presence of 0.79 g (0.0057 mole) of anhydrous potassium carbonate in 25 mL of N,N-dimethylformamide, yielding 1.54 g of methyl 2-[3-[4-(4-difluoromethyl-4,5-dihydro-3-methyl-1,2,4-triazol-5(1H)-on-1-yl)-3-fluorophenoxymethyl]phenoxy]propionate. The NMR and IR spectra were consistent with the proposed structure. NMR: 1.60 (d, 3H, $J_{HH}=8.0$ Hz); 2.44 (s, 3H); 3.76 (s, 3H); 4.78 (q, 1H, $J_{HH}=8.0$ Hz); 5.04 (s, 2H); 6.76–7.38 (m, 8H).

EXAMPLE 10

METHYL 2-[4-[4-(4-DIFLUOROMETHYL-4,5-DIHYDRO-3-METHYL-1,2,4-TRIAZOL-5(1H)-ON-1-YL)-3-FLUOROPHENOXYMETHYL]PHENOXY]PROPIONATE (Compound 81)

Step A Methyl 2-(4-formylphenoxy)propionate

By the method of Example 1, Step H, 10.0 g (0.0819 mole) of 4-hydroxybenzaldehyde and 16.4 g (0.0983 mole) of methyl 2-bromopropionate were reacted in the presence of 13.6 g (0.0983 mole) of anhydrous potassium carbonate in N,N-dimethylformamide, yielding 12.2 g of methyl 2-(4-formylphenoxy)propionate as a yellow liquid. The NMR and IR spectra were consistent with the proposed structure.

Step B Methyl 2-(4-hydroxymethylphenoxy)propionate

By the method of Example 1, Step I, 11.1 g (0.0533 mole) of methyl 2-(4-formylphenoxy)propionate and 2.02 g (0.0533 mole) of sodium borohydride were reacted in methanol, yielding 9.31 g of methyl 2-(4-hydroxymethylphenoxy)propionate as a yellow oil. The NMR spectrum was consistent with the proposed structure.

Step C Methyl 2-(4-chloromethylphenoxy)propionate

A mixture of 2.19 g (0.0104 mole) of methyl 2-(4-hydroxymethylphenoxy)propionate and 3.00 g (0.0823 mole) of 36% hydrochloric acid was stirred for fifteen minutes at room temperature. The reaction mixture was then poured into ice-water, and the resulting mixture was extracted with diethyl ether. The extracts were combined and washed in succession with water and a saturated aqueous solution of sodium bicarbonate. The extract was dried over anhydrous magnesium sulfate and filtered, and the solvent was evaporated from the filtrate under reduced pressure, leaving a colorless liquid. This liquid was placed on a column of silica gel and eluted with methylene chloride. After the product-containing fractions were combined and the solvent evaporated under reduced pressure, 1.6 g of methyl 2-(4-chloromethylphenoxy)propionate was isolated as a colorless liquid. The NMR and IR spectra were consistent with the proposed structure.

Step D Methyl 2-[4-[4-(4-difluoromethyl-4,5-dihydro-3-methyl-1,2,4-triazol-5(1H)-on-1-yl)-3-fluorophenoxymethyl]phenoxy]propionate By the method of Example 1, Step K, 0.50 g (0.0019 mole) of 1-(2-fluoro-4-hydroxyphenyl)-4-difluoromethyl-4,5-dihydro-3-methyl-1,2,4-triazol-5(1H)-one (Example 1, Step F) and 0.87 g (0.0038 mole) of methyl 2-(4-chloromethylphenoxy)propionate were reacted in the presence of 0.2 g of 1,4,7,10,13,16-hexaoxacyclooctadecane in 25 mL of N,N-dimethylformamide, yielding 0.80 g of methyl 2-[4-[4-(4-difluoromethyl-4,5-dihydro-3-methyl-1,2,4-triazol-5(1H)-on-1-yl)-3-fluorophenoxymethyl] phenoxy]propionate as a colorless oil that solidified upon standing, m.p. 83°-85° C. The NMR and IR spectra were consistent with the proposed structure. NMR: 1.60 (d, 3H, $J_{HH}=8.0$ Hz); 2.44 (s, 3H); 3.76 (s, 3H); 4.78 (q, 1H, $J_{HH}=8.0$ Hz); 4.90 (s, 2H); 6.78–7.38 (m, 8H).

EXAMPLE 11

METHYL 2-[2-[4-(8-THIA-1,6-DIAZABICYCLO[4.3.0]NONANE-7-ON-9-YLIMINO)-3-FLUOROPHENOXYMETHYL]-5-METHYLPHENOXY]PROPIONATE (Compound 68)

Step A Methyl 2-[2-(3-fluoro-4-nitrophenoxymethyl)-5-methylphenoxy]propionate

By the method of Example 1, Step K, 1.71 g (0.010 mole) of 3-fluoro-4-nitrophenol and 2.85 g (0.011 mole) of methyl 2-(2-chloromethyl-5-methylphenoxy)propionate were reacted in the presence of 1.66 g (0.012 mole) of anhydrous potassium carbonate in 100 mL of N,N-dimethylformamide, yielding 3.55 g of methyl 2-[2-(3-fluoro-4-nitrophenoxymethyl)-5-methylphenoxy]propionate as a yellowish solid, m.p. 92°-94° C. The NMR and IR spectra were consistent with the proposed structure.

Step B Methyl 2-[2-(4-amino-3-fluorophenoxymethyl)-5-methylphenoxy]propionate

By the method of Example 2, Step A, 3.35 g (0.0091 mole) of methyl 2-[2-(3-fluoro-4-nitrophenoxymethyl)-5-methylphenoxy]propionate was reacted with 2.80 g (0.050 mole) of powdered iron in 100 mL of acetic acid, yielding 1.86 g of methyl 2-[2-(4-amino-3-fluorophenoxymethyl)-5-methylphenoxy]propionate as an amber syrup. The NMR and IR spectra were consistent with the proposed structure.

Step C Methyl 2-[2-(3-fluoro-4-isothiocyanatophenoxymethyl)-5-methylphenoxy]propionate A solution of 1.66 g (0.005 mole) of methyl 2-[2-(4-amino-3-fluorophenoxymethyl)-5-methylphenoxy]propionate and 1.26 g (0.0125 mole) of triethylamine in 40 mL of methylene chloride was prepared at ambient temperature. To this solution was added dropwise a solution of 0.58 g (0.0050 mole) of thiophosgene in 10 mL of methylene chloride. The reaction mixture was stirred for 16 hours after which it was filtered through a short column of silica gel. The solvent was evaporated from the filtrate under reduced pressure, leaving 1.50 g of methyl 2-[2-(3-fluoro-4-isothiocyanatophenoxymethyl)-5-methylphenoxy]propionate as a syrup. The NMR and IR spectra were consistent with the proposed structure.

Step D Methyl 2-[2-[4-(perhydropyridazin-1-ylthiocarbonylamino)-3-fluorophenoxymethyl]-5-methylphenoxy]propionate By the method of Example 1, Step C, of U.S. Pat. No. 4,906,281, 1.50 g (0.004 mole) of methyl 2-[2-(3-fluoro-4-isothiocyanatophenoxymethyl)-5-methylphenoxy]propionate and 1.07 g (0.005 mole) of perhydropyridazine monohydroiodide (prepared by the method of Example 1, Step B, of U.S. Pat. No. 4,906,281) were reacted in the presence of 0.20 g (0.0050 mole of sodium hydroxide in 40 mL of water and 10 ML of tetrahydrofuran, yielding 1.50 g of methyl 2-[2-[4-(perhydropyridazin-1-ylthiocarbonylamino)-3-fluorophenoxymethyl]-5-methylphenoxy]propionate as a syrup. The NMR spectrum was consistent with proposed structure.

Step E Methyl 2-[2-[4-(8-thia-1,6-diazabicyclo[4.3.0-]nonane-7-on-9-ylimino)-3-fluorophenoxymethyl]-5-methylphenoxy]propionate By the method of Example 1, Step D, of U.S. Pat. No. 4,906,281, 1.50 g (0.00325 mole) of methyl 2-[2-[4-(perhydropyridazin-1-ylthiocarbonylamino)-3-fluorophenoxymethyl]-5-methylphenoxy]propionate and 0.36 g (0.09017 mole) of trichloromethyl chloroformate were reacted in the presence of 0.36 g (0.0035 mole) of triethylamine in 35 mL of dioxane, yielding 0.50 g of methyl 2-[2-[4-(8-thia-1,6-diazabicyclo[4.3.0]nonane-7-on-9-ylimino)-3-fluorophenoxymethyl]-5-methylphenoxy]propionate as a syrup. The NMR and IR spectra were consistent with the proposed structure. NMR: 1.60 (d, 3H, $J_{HH}=8.0$ Hz); 1.78–1.96 (m, 4H); 2.30 (s, 3H); 3.64–3.80 (m, 4H): 3.70 (s, 3H); 4.80 (q, 1H, $J_{HH}=8.0$ Hz); 5.10 dd, 2H); 6.58–7.30 (m, 6H).

Representative compounds of the invention prepared by the methods exemplified above are shown in Table 1.

HERBICIDAL ACTIVITY

The 2-[(4-heterocyclic-substituted-3-halophenoxymethyl)phenoxy]alkanoates of this invention were tested in pre- and postemergence evaluations using a variety of broadleaf and grasseous crops and weeds. The test species used to demonstrate the herbicidal activity of these compounds include soybean (Glycine max var. Williams), field corn (Zea mays var. Agway 425X), wheat (Triticum aestivum var. Wheaton), morningglory (Ipomea lacunosa or Ipomea hederacea), velvetleaf (Abutilon theophrasti), green foxtail (Setaria viridis), Johnsongrass (Sorphum halepense), blackgrass (Alopecurus myosuroides), common chickweed (Stellaria media), and common cocklebur (Xanthium pensylvanicum).

Preparation of Flats

For preemergence testing two disposable fiber flats (8 cm × 15 cm × 25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner, except that they were planted 8–12 days prior to the preemergence flats and were placed in a greenhouse and watered, thus allowing the seeds to germinate and the foliage to develop.

A stock solution of the candidate herbicide was prepared by dissolving a predetermined weight of the compound in 20 ml of water/acetone (50/50) containing 0.5% v/v sorbitan monolaurate. Thus for an application rate of 3000 g/ha of herbicide, 0.21 g of candidate herbicide was dissolved in 20 ml of the aqueous acetone to prepare the stock solution. For the 300 g/ha rate of application used in most of the tests reported below, a 1.0 mL portion of stock solution was diluted with water/acetone (50/50) to 35 ml, the volume required for a spray volume of 1000 L/ha. The remaining stock solution was then used to prepare spray solutions for other application rates.

The spray solution (35 ml) was then sprayed on the four flats simultaneously, i.e., to the surface of the soil of the preemergence flats and to the emerged foliage of the postemergence flats. All flats were placed in the greenhouse, but only the preemergence flats were watered immediately. The foliage of the postemergence flats was kept dry for 24 hours, after which regular watering commenced. Phytotoxicity data, taken as percent control, were recorded 17–21 days after the chemical was applied.

Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
| --- | --- | --- | --- |
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data at 300 or 250 presented in Table 2 (preemergence activity) and Table 3 (post-emergence activity). The test compounds are identified in Tables 2 and 3 by numbers which correspond to those in Table 1.

For herbicidal application the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile liquid such as water, corn oil, kerosene, propylene glycol, or other suitable liquid carrier.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 10 to 100 g/ha, preferably about 30 to 60 g/ha. For field use, where there are losses of herbicide, higher application rates (e.g., four times the greenhouse testing rates mentioned above) may be employed.

The active herbicidal compounds of this invention may be used in combination with other herbicides, e.g. they may be mixed with, say, a lesser, equal, or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl-)acetamide (metolachlor), and N-chloroacetyl-N-(2,6-diethylphenyl)glycine (diethatyl ethyl); benzothiadiazinone herbicides such as 3-(1-methylethyl)-(1H)-2,1,3-benzothiadiazin-4-(3H)-one-2,2-dioxide (bentazon): triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

| Compound No. | $Q^a$ | X | Y | Z | Z' | R |
|---|---|---|---|---|---|---|

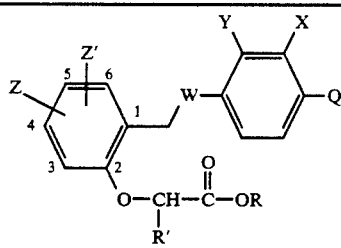

| | | | R' = CH$_3$, W = O | | | |
|---|---|---|---|---|---|---|
| 1 | A | H | H | H | H | CH$_3$ |
| 2 | A | F | H | H | H | H |
| 3 | A | F | H | H | H | CH$_3$ |
| 4 | A | F | H | 4-F | H | CH$_3$ |
| 5 | A | F | H | 3-Cl | H | CH$_3$ |
| 6 | A | F | H | 4-Cl | H | H |
| 7 | A | F | H | 4-Cl | H | CH$_3$ |
| 8 | A | F | H | 5-Cl | H | CH$_3$ |
| 9 | A | F | H | 4-Br | H | CH$_3$ |
| 10 | A | F | H | 3-F | 4-F | CH$_3$ |
| 11 | A | F | H | 3-Cl | 4-Cl | CH$_3$ |
| 12 | A | F | H | 4-CH$_3$ | H | CH$_3$ |
| 13 | A | F | H | 5-OCH$_3$ | H | CH$_3$ |
| 14 | A | Cl | H | H | H | CH$_3$ |
| 15 | A | Cl | H | H | H | CH$_3$O(CH$_2$)$_2$O(CH$_2$)$_2$ |

TABLE 1-continued

| | | | | | | |
|---|---|---|---|---|---|---|
| 16 | A | Cl | H | 4-F | H | CH₃ |
| 17 | A | Cl | H | 3-Cl | H | CH₃ |
| 18 | A | Cl | H | 4-Cl | H | CH₃ |
| 19 | A | Cl | H | 4-Br | H | CH₃ |
| 20 | A | Cl | H | 3-F | 4-F | CH₃ |
| 21 | A | Cl | H | 3-Cl | 4-Cl | CH₃ |
| 22 | A | Cl | H | 4-CH₃ | H | CH₃ |
| 23 | B | H | H | H | H | CH₃ |
| 24 | B | F | H | H | H | CH₃ |
| 25 | B | F | H | 4-F | H | CH₃ |
| 26 | B | F | H | 3-Cl | H | CH₃ |
| 27 | B | F | H | 4-Cl | H | CH₃ |
| 28 | B | F | H | 5-Cl | H | CH₃ |
| 29 | B | F | H | 4-Br | H | CH₃ |
| 30 | B | F | H | 3-F | 4-F | CH₃ |
| 31 | B | F | H | 3-Cl | 4-Cl | CH₃ |
| 32 | B | F | H | 4-CH₃ | H | CH₃ |
| 33 | B | Cl | H | 4-F | H | CH₃ |
| 34 | B | Cl | H | 3-Cl | H | CH₃ |
| 35 | B | Cl | H | 4-Cl | H | CH₃ |
| 36 | B | Cl | H | 4-Br | H | CH₃ |
| 37 | B | Cl | H | 3-Cl | 4-Cl | CH₃ |
| 38 | B | Cl | H | 4-CH₃ | H | CH₃ |
| 39 | B | 3-OC(CH₃)₂CH₂-2 | H | H | H | CH₃ |
| 40 | B | 3-OC(CH₃)₂CH₂-2 | H | 4-Cl | H | CH₃ |
| 41 | C | F | H | H | H | CH₃ |
| 42 | C | F | H | 4-F | H | CH₃ |
| 43 | C | F | H | 3-Cl | H | CH₃ |
| 44 | C | F | H | 4-Cl | H | CH₃ |
| 45 | C | F | H | 3-Cl | 4-Cl | CH₃ |
| 46 | A | F | H | 4-Cl | 6-Cl | CH₃ |
| 47 | A | F | H | 4-CH₃ | H | H |
| 48 | A | F | H | 4-CH₃ | H | C₂H₅ |
| 49 | A | F | H | 4-CH₃ | H | i-C₃H₇ |
| 50 | A | F | H | 4-C₂H₅ | H | H |
| 51 | A | F | H | 4-C₂H₅ | H | CH₃ |
| 52 | A | F | H | 4-C₃H₇ | H | CH₃ |
| 53 | A | F | H | 4-i-C₃H₇ | H | CH₃ |
| 54 | A | F | H | 4-C₄H₉ | H | CH₃ |
| 55 | A | F | H | 4-t-C₄H₉ | H | CH₃ |
| 56 | A | F | H | 4-C₂H₅ | H | CH₃OCH₂CH(CH₃) |
| 57 | A | F | H | 4-CH₃ | H | CH₃O(CH₂)₂O(CH₂)₂ |
| 58 | A | F | H | 4-C₂H₅ | H | CH₃O(CH₂)₂O(CH₂)₂ |
| 59 | A | F | H | 4-t-C₄H₉ | H | CH₃O(CH₂)₂O(CH₂)₂ |
| 60 | A | F | H | 4-φ | H | CH₃ |
| 61 | A | F | H | 3-(CH₂)₄-4 | | CH₃ |
| 62 | A | Cl | H | 4-C₂H₅ | H | CH₃ |
| 63 | D | F | H | 4-Cl | H | CH₃ |
| 64 | D | F | H | 4-CH₃ | H | CH₃ |
| 65 | D | F | H | 4-C₂H₅ | H | CH₃ |
| 66 | E | F | H | 4-Cl | H | CH₃ |
| 67 | E | F | H | 4-CH₃ | H | CH₃ |
| 68 | F | F | H | 4-CH₃ | H | CH₃ |
| 69 | G | F | H | 4-Cl | H | CH₃ |
| 70 | G | F | H | 4-CH₃ | H | CH₃ |
| 71 | G | F | H | 4-C₃H₇ | H | CH₃ |
| R' = CH₃, W = S | | | | | | |
| 72 | A | F | H | 4-Cl | H | CH₃ |
| 73 | A | F | H | 4-CH₃ | H | CH₃ |
| R' = H, W = O | | | | | | |
| 74 | A | F | H | H | H | CH₃ |
| 75 | A | F | H | 4-CH₃ | H | CH₃ |
| 76 | A | F | H | 4-CH₃ | H | H |
| 77 | B | F | H | H | H | CH₃ |
| 78 | D | F | H | 4-CH₃ | H | CH₃ |

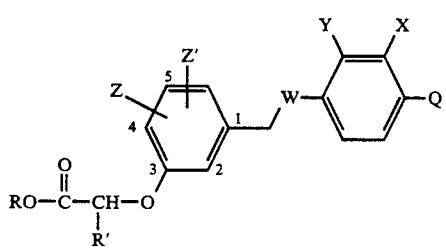

R' = CH₃, W = O

| | | | | | | |
|---|---|---|---|---|---|---|
| 79 | A | F | H | H | H | H |
| 80 | A | F | H | H | H | CH₃ |

TABLE 1-continued
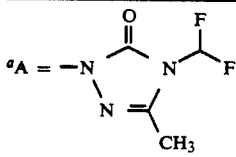
R' = CH₃, W = O
| 81 | A | F | H | H | H | CH₃ |
| 82 | A | F | H | H | H | CH₃O(CH₂)₂O(CH₂)₂ |
| 83 | A | Cl | H | H | H | CH₃ |
| 84 | B | F | H | H | H | CH₃ |
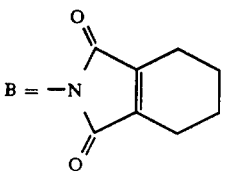
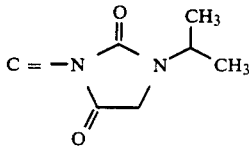
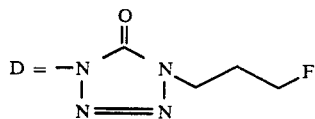
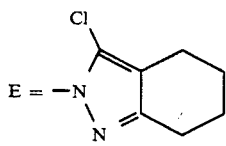
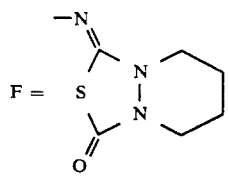
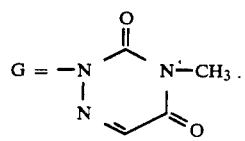
G = 
TABLE 2
PREEMERGENCE HERBICIDAL ACTIVITY (% Control)
| | Compound No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14* |
| Species | Rate (kg/ha) | | | | | | | | | | | | | |
| | 0.3 | 0.3 | 0.25 | 0.3 | 0.3 | 0.3 | 0.3 | 0.3 | 0.3 | 0.3 | 0.3 | 0.3 | 0.3 | 0.3 |
| Soybean | 0 | 0 | 90 | 80 | 10 | 10 | 50 | 0 | 100 | 10 | 0 | 20 | 0 | 0 |
| Wheat | 70 | 80 | 20 | 80 | 10 | 50 | 95 | 0 | 80 | 20 | 10 | 70 | 0 | 5 |
| Corn | 15 | 15 | 15 | 70 | 20 | 85 | 10 | 5 | 95 | 10 | 10 | 50 | 5 | 10 |
| Velvetleaf | 100 | 100 | 100 | 100 | 100 | 100 | 100 | 85 | 100 | 100 | 100 | 100 | 100 | 85 |

TABLE 2-continued

| | | | | | | | | | | | | | |
|---|---|---|---|---|---|---|---|---|---|---|---|---|---|
| Morningglory | 100 | 100 | 100 | 100 | 100 | 100 | 100 | 85 | 100 | 95 | 100 | 100 | 60 | 70 |
| Chickweed | 90 | 80 | 90 | 100 | 100 | 100 | 100 | 90 | 100 | 100 | 100 | 100 | 20 | 45 |
| Cocklebur | 10 | 20 | 70 | 80 | 70 | 100 | 100 | 0 | 100 | 40 | 60 | 90 | 30 | 0 |
| Blackgrass | 80 | 40 | 70 | 95 | 90 | 100 | 100 | 0 | 100 | 70 | 20 | 80 | 0 | 0 |
| Green foxtail | 90 | 80 | 100 | 100 | 100 | 100 | 100 | 10 | 100 | 100 | 100 | 100 | 85 | 75 |
| Johnsongrass | 80 | 70 | 70 | 95 | 95 | 80 | 70 | 40 | 95 | 40 | 90 | 60 | 10 | 30 |

*Average of two tests - where average is not a multiple of five, given as next lower multiple of five.

| | Compound No. | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.25 | 0.3 | 0.3 | 0.3 | 0.3 |
| Soybean | 0 | 10 | 10 | 0 | 60 | 0 | 0 | 10 | — | 5 | 20 | 0 | 10 | 90 |
| Wheat | 5 | 10 | 70 | 10 | — | 0 | 0 | 60 | 5 | 10 | 20 | 0 | 0 | 95 |
| Corn | 5 | 15 | 10 | 30 | 20 | 0 | 30 | 50 | 5 | 5 | 10 | 0 | 15 | 95 |
| Velvetleaf | 100 | 100 | 100 | 100 | 100 | 100 | 100 | 100 | 30 | 80 | 100 | 85 | 100 | 50 |
| Morningglory | 100 | 100 | 30 | 90 | 90 | 80 | 70 | 90 | 100 | 70 | 100 | 95 | 100 | 20 |
| Chickweed | 90 | 100 | 40 | 100 | 100 | 50 | 20 | 80 | 85 | 95 | 100 | — | 100 | 85 |
| Cocklebur | 5 | 60 | 20 | 40 | 60 | 0 | 20 | 10 | 0 | 20 | 80 | 10 | 80 | 0 |
| Blackgrass | 0 | 20 | 80 | 10 | 90 | 10 | 10 | 30 | 5 | 90 | 0 | 40 | 70 | 60 |
| Green foxtail | 50 | 100 | 90 | 100 | 100 | 100 | 95 | 95 | 40 | 30 | 60 | 20 | 0 | 15 |
| Johnsongrass | 0 | 60 | 95 | 90 | 90 | 60 | 70 | 50 | 60 | 15 | 10 | 0 | 40 | 85 |

| | Compound No. | | | | | | | | | | | | | |
|---|---|---|---|---|---|---|---|---|---|---|---|---|---|---|
| | 29 | 30 | 31 | 32 | 33 | 34 | 35 | 36 | 37 | 38 | 39 | 40 | 41 | 42 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 90 | 40 | 10 | 30 | 0 | 0 | 0 | 0 | 0 | 0 | 10 | 10 | 0 | 0 |
| Wheat | 0 | 0 | 0 | 0 | 0 | 0 | 0 | 0 | 0 | 0 | — | 10 | 0 | 0 |
| Corn | 20 | 0 | 0 | 0 | 15 | 0 | 10 | 0 | 0 | 0 | — | 0 | 0 | 50 |
| Velvetleaf | 100 | 100 | 100 | 100 | 100 | 95 | 100 | 100 | 80 | 70 | 0 | 0 | — | 0 |
| Morningglory | 100 | 90 | 95 | 100 | 100 | 90 | 95 | 80 | 60 | 20 | 10 | 0 | 10 | 0 |
| Chickweed | 100 | 95 | 10 | 100 | 100 | — | 95 | 100 | 0 | 50 | — | 100 | 0 | 0 |
| Cocklebur | 85 | 100 | 20 | 80 | 10 | 10 | 10 | 20 | 0 | 10 | 0 | 10 | 10 | 20 |
| Blackgrass | — | 30 | 10 | 30 | 0 | 10 | 10 | 10 | 0 | 0 | 0 | 0 | 0 | 0 |
| Green foxtail | 95 | 70 | 0 | 100 | 70 | 0 | 0 | 10 | 10 | 40 | — | 0 | 10 | 0 |
| Johnsongrass | 80 | 10 | 10 | 10 | 10 | 0 | 0 | 20 | 0 | 10 | 10 | 20 | 10 | 30 | 0 |

| | Compound No. | | | | | | | | | | | | | |
|---|---|---|---|---|---|---|---|---|---|---|---|---|---|---|
| | 43 | 44 | 45 | 46 | 47 | 48 | 49 | 50 | 51 | 52 | 53 | 54 | 55 | 56 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 0 | 20 | 0 | 20 | 30 | 90 | 75 | 60 | 80 | 90 | 100 | 95 | 70 | 90 |
| Wheat | 0 | 0 | 0 | 10 | 75 | 90 | 85 | 75 | 80 | 20 | 80 | 0 | 20 | 50 |
| Corn | 30 | 20 | 0 | 10 | 75 | 90 | 75 | 30 | 75 | 60 | 40 | 30 | 30 | 40 |
| Velvetleaf | 0 | 80 | 0 | 100 | 100 | 100 | 100 | 100 | 100 | 100 | 100 | 100 | 100 | 100 |
| Morningglory | 0 | 80 | — | 95 | 100 | 100 | 100 | 85 | 100 | 100 | 100 | 100 | 100 | 100 |
| Chickweed | 0 | 80 | 0 | 100 | 100 | 100 | 100 | 100 | 100 | 100 | 100 | 100 | 100 | 100 |
| Cocklebur | 0 | 70 | — | 60 | 75 | 100 | 100 | 75 | 85 | 95 | 90 | 50 | 80 | 75 |
| Blackgrass | 0 | 10 | 0 | 40 | 95 | 95 | 90 | 80 | 80 | 40 | 100 | 20 | 75 | 75 |
| Green foxtail | 0 | 20 | 0 | 100 | 100 | 100 | 100 | 100 | 100 | 100 | 100 | 95 | 95 | 100 |
| Johnsongrass | 20 | 30 | 0 | 90 | 75 | 90 | 100 | 80 | 95 | 90 | 70 | 70 | 75 | 95 |

| | Compound No. | | | | | | | | | | | | | |
|---|---|---|---|---|---|---|---|---|---|---|---|---|---|---|
| | 57 | 58 | 59 | 60 | 61 | 62 | 63 | 64 | 65 | 66 | 67 | 68 | 69 | 70 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 40 | 60 | 50 | 75 | 40 | 40 | 40 | 30 | 85 | 10 | 10 | 40 | 60 | 20 |
| Wheat | 80 | 75 | 20 | 20 | 20 | 70 | 10 | 20 | 10 | 10 | 10 | 10 | 40 | 40 |
| Corn | 75 | 40 | 20 | 20 | 20 | 50 | 10 | 30 | 10 | 0 | 10 | 10 | 20 | 50 |
| Velvetleaf | 100 | 100 | 100 | 100 | 100 | 100 | 100 | 100 | 100 | 80 | 100 | 100 | 100 | 100 |
| Morningglory | 95 | 100 | 85 | 100 | 80 | 100 | 100 | 90 | 100 | 10 | 100 | 90 | 100 | 100 |
| Chickweed | 100 | 100 | 90 | 100 | 70 | 100 | 100 | 100 | 100 | 0 | 60 | 100 | 100 | 100 |
| Cocklebur | 70 | 30 | 75 | 60 | 10 | 60 | 75 | 60 | 80 | 10 | 30 | 40 | 90 | 30 |
| Blackgrass | 80 | 75 | 70 | 60 | 40 | 85 | 70 | 30 | 50 | 30 | 60 | 30 | 40 | 0 |
| Green foxtail | 100 | 100 | 90 | 100 | 100 | 100 | 100 | 50 | 100 | 0 | 75 | 80 | 100 | 100 |
| Johnsongrass | 80 | 90 | 80 | 70 | 70 | 80 | 75 | 30 | 80 | 0 | 10 | 40 | 95 | 20 |

| | Compound No. | | | | | | | | | | | | | |
|---|---|---|---|---|---|---|---|---|---|---|---|---|---|---|
| | 71 | 72 | 73 | 74 | 75 | 76 | 77 | 78 | 79 | 80 | 81 | 82 | 83 | 84 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.25 | 0.25 | 0.3 | 0.25 |
| Soybean | 85 | 40 | 0 | 10 | 10 | 20 | 10 | 10 | 0 | 0 | 0 | 0 | 0 | 10 |
| Wheat | 20 | 40 | 0 | 80 | 60 | 60 | 5 | 20 | 10 | 85 | 0 | 5 | 5 | 0 |
| Corn | 30 | 60 | 0 | 20 | 20 | 70 | 10 | 10 | 20 | 5 | 10 | 40 | 5 | 5 |
| Velvetleaf | 100 | 100 | 100 | 100 | 100 | 100 | 10 | 100 | 100 | 100 | 50 | 95 | 0 | 0 |
| Morningglory | 100 | 95 | 80 | 100 | 100 | 100 | 80 | 100 | 95 | 100 | 80 | 85 | 0 | 10 |
| Chickweed | 100 | 100 | 100 | 80 | 75 | 80 | 20 | 30 | 95 | 90 | 15 | 30 | 90 | 5 |
| Cocklebur | 85 | 75 | 20 | 0 | 10 | 30 | 10 | 60 | 0 | 20 | 20 | 40 | 0 | 5 |
| Blackgrass | 0 | 75 | 70 | 95 | 75 | 60 | 5 | 30 | 40 | 50 | 60 | 60 | 0 | 0 |

TABLE 2-continued

| | | | | | | | | | | | | | | |
|---|---|---|---|---|---|---|---|---|---|---|---|---|---|---|
| Green foxtail | 100 | 90 | 100 | 80 | 100 | 100 | 20 | 80 | 70 | 100 | 95 | 85 | — | 30 |
| Johnsongrass | 75 | 50 | 30 | 70 | 70 | 80 | 20 | 50 | 95 | 80 | 10 | 80 | 5 | 10 |

TABLE 3

POSTEMERGENCE HERBICIDAL ACTIVITY (% Control)

| | Compound No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14* |
| | Rate (kg/ha) | | | | | | | | | | | | | |
| Species | 0.3 | 0.3 | 0.25 | 0.3 | 0.3 | 0.3 | 0.3 | 0.3 | 0.3 | 0.3 | 0.3 | 0.3 | 0.3 | 0.3 |
| Soybean | 60 | 85 | 95 | 95 | 80 | 90 | 95 | 40 | 100 | 95 | 80 | 95 | 70 | 50 |
| Wheat | 85 | 100 | 95 | 100 | 95 | 100 | 100 | 20 | 100 | 100 | 95 | 100 | 20 | 50 |
| Corn | 70 | 100 | 95 | 100 | 100 | 100 | 100 | 40 | 100 | 100 | 100 | 100 | 75 | 75 |
| Velvetleaf | 100 | 100 | 100 | 100 | 100 | 100 | 100 | 70 | 100 | 100 | 100 | 100 | 80 | 100 |
| Morningglory | 100 | 100 | 100 | 100 | 100 | 100 | 100 | 100 | 100 | 100 | 100 | 100 | 60 | 100 |
| Chickweed | 90 | — | 100 | 100 | 100 | 100 | 100 | 100 | 100 | 95 | 100 | 100 | 0 | 5 |
| Cocklebur | 50 | 100 | 100 | 100 | 100 | 100 | 100 | 40 | 100 | 95 | 100 | — | 60 | 55 |
| Blackgrass | 30 | 90 | 95 | 100 | 40 | 100 | 100 | 0 | 100 | 100 | 95 | 100 | 5 | 10 |
| Green foxtail | 100 | 100 | 100 | 100 | 100 | 100 | 100 | 70 | 100 | 100 | 100 | 100 | 20 | 90 |
| Johnsongrass | 80 | 100 | 90 | 100 | 95 | 100 | 90 | 10 | 100 | 95 | 100 | 100 | 40 | 35 |

*Average of two tests - where average is not a multiple of five, given as next lower multiple of five.

| | Compound No. | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.25 | 0.3 | 0.3 | 0.3 | 0.3 |
| Soybean | 50 | 75 | 60 | 85 | 60 | 70 | 30 | 70 | 40 | 90 | 75 | 60 | 95 | 95 |
| Wheat | 95 | 100 | 30 | 100 | 100 | 95 | 20 | 100 | 15 | 20 | 10 | 20 | 15 | 90 |
| Corn | 95 | 95 | 95 | 100 | 100 | 100 | 30 | 90 | 30 | 100 | 75 | 75 | 100 | 80 |
| Velvetleaf | 100 | 100 | 100 | 100 | 100 | 100 | 95 | 100 | 80 | 100 | 100 | 60 | 100 | 90 |
| Morningglory | 100 | 100 | 95 | 100 | 100 | 100 | 100 | 100 | 100 | 100 | 100 | 100 | 100 | 95 |
| Chickweed | 10 | 100 | 20 | 100 | 100 | 80 | 20 | 95 | 40 | 100 | 100 | 20 | 100 | 95 |
| Cocklebur | 60 | 100 | 80 | 100 | 100 | 90 | 80 | — | 20 | 100 | 100 | 100 | 100 | 70 |
| Blackgrass | 5 | 60 | 10 | 95 | 100 | 70 | 20 | 95 | 5 | 60 | 0 | 0 | 10 | 85 |
| Green foxtail | 100 | 100 | 30 | 100 | 100 | 100 | 95 | 100 | 15 | 85 | 80 | 0 | 90 | 20 |
| Johnsongrass | 70 | 95 | 85 | 100 | 95 | 100 | 90 | 70 | 10 | 70 | 95 | 10 | 50 | 40 |

| | Compound No. | | | | | | | | | | | | | |
|---|---|---|---|---|---|---|---|---|---|---|---|---|---|---|
| | 29 | 30 | 31 | 32 | 33 | 34 | 35 | 36 | 37 | 38 | 39 | 40 | 41 | 42 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 90 | 90 | 40 | 95 | 70 | 10 | 60 | 40 | 30 | 20 | 10 | 0 | 30 | 70 |
| Wheat | 30 | 20 | 15 | 10 | 0 | 10 | 15 | 0 | 15 | 0 | 0 | 0 | 0 | 10 |
| Corn | 80 | 80 | 100 | 80 | 50 | 25 | 25 | 80 | 10 | 60 | 10 | 15 | 30 | 40 |
| Velvetleaf | 100 | 100 | 100 | 100 | 100 | 50 | 100 | 100 | 85 | 80 | 10 | 0 | 100 | 85 |
| Morningglory | 100 | 95 | 100 | 100 | 100 | 90 | 100 | 100 | 50 | 100 | 0 | 0 | 100 | 100 |
| Chickweed | 100 | 95 | 30 | 100 | 80 | 0 | 100 | 95 | 10 | 80 | 20 | 0 | — | 70 |
| Cocklebur | 90 | 100 | 85 | — | 80 | 10 | 80 | 95 | 60 | — | 0 | 0 | — | 90 |
| Blackqrass | 0 | 10 | 0 | 0 | 10 | 0 | 0 | 0 | 10 | 0 | 0 | 0 | 0 | 0 |
| Green foxtail | 50 | 80 | 80 | 60 | 20 | 0 | 50 | 30 | 10 | 30 | 20 | 0 | 20 | 30 |
| Johnsongrass | 0 | 60 | 30 | 20 | 0 | 0 | 50 | 0 | 4 | 0 | 0 | 0 | 50 | 30 |

| | Compound No. | | | | | | | | | | | | | |
|---|---|---|---|---|---|---|---|---|---|---|---|---|---|---|
| | 43 | 44 | 45 | 46 | 47 | 48 | 49 | 50 | 51 | 52 | 53 | 54 | 55 | 56 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 30 | 80 | 50 | 60 | 80 | 95 | 75 | 95 | 100 | 100 | 100 | 100 | 90 | 90 |
| Wheat | 0 | 40 | 0 | 90 | 95 | 100 | 95 | 90 | 95 | 100 | 100 | 60 | 70 | 95 |
| Corn | 0 | 70 | 40 | 75 | 100 | 100 | 50 | 90 | 100 | 100 | 80 | 70 | 50 | 60 |
| Velvetleaf | 70 | 100 | 60 | 100 | 100 | 100 | 100 | 100 | 100 | 100 | 100 | 100 | 100 | 100 |
| Morningglory | 85 | 100 | 80 | 100 | 100 | 100 | 100 | 100 | 100 | 100 | 100 | 100 | 100 | 100 |
| Chickweed | 0 | 90 | 0 | 100 | 100 | 100 | 100 | 100 | 100 | 100 | 100 | 100 | 95 | 100 |
| Cocklebur | 60 | 100 | 95 | 100 | 100 | 100 | 100 | 100 | 100 | 100 | 100 | 100 | 100 | 100 |
| Blackgrass | 0 | 0 | 0 | 80 | 100 | 100 | 100 | 100 | 100 | 85 | 100 | 60 | 90 | 95 |
| Green foxtail | 10 | 20 | 30 | 100 | 100 | 100 | 100 | 100 | 100 | 100 | 100 | 100 | 100 | 100 |
| Johnsongrass | 30 | 10 | 70 | 100 | 100 | 100 | 100 | 100 | 95 | 100 | 100 | 100 | 95 | 100 |

| | Compound No. | | | | | | | | | | | | | |
|---|---|---|---|---|---|---|---|---|---|---|---|---|---|---|
| | 57 | 58 | 59 | 60 | 61 | 62 | 63 | 64 | 65 | 66 | 67 | 68 | 69 | 70 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.3 | 0.3 | 0.3 | 0.3 |
| Soybean | 80 | 95 | 90 | 100 | 95 | 85 | 85 | 75 | 95 | 40 | 40 | 95 | 80 | 80 |
| Wheat | 85 | 100 | 95 | 90 | 40 | 90 | 80 | 85 | 90 | 0 | 10 | 20 | 100 | 100 |
| Corn | 100 | 100 | 60 | — | 60 | 80 | 75 | 60 | 70 | 20 | 20 | 60 | 100 | 100 |
| Velvetleaf | 100 | 100 | 100 | 100 | 100 | 100 | 100 | 100 | 100 | 95 | 100 | 100 | 100 | 100 |
| Morningglory | 100 | 100 | 100 | 100 | 100 | 100 | 100 | 100 | 100 | 80 | 100 | 100 | 100 | 100 |
| Chickweed | 100 | 100 | 100 | 100 | 100 | 100 | 100 | 100 | 100 | 95 | 100 | 100 | 100 | 100 |
| Cocklebur | 100 | 95 | 100 | 100 | 100 | 100 | 100 | 100 | 100 | 100 | 100 | 100 | 100 | 100 |

TABLE 3-continued

| | | | | | | | | | | | | | | |
|---|---|---|---|---|---|---|---|---|---|---|---|---|---|---|
| Blackgrass | 95 | 100 | 90 | 75 | 70 | 95 | 75 | 80 | 85 | 10 | 10 | 70 | 95 | 80 |
| Green foxtail | 100 | 100 | 100 | 100 | 100 | 100 | 100 | 100 | 100 | 95 | 80 | 100 | 100 | 100 |
| Johnsongrass | 100 | 100 | 100 | 100 | 100 | 100 | 95 | 90 | 100 | — | 70 | 95 | 100 | 100 |
| | Compound No. | | | | | | | | | | | | | |
| | 71 | 72 | 73 | 74 | 75 | 76 | 77 | 78 | 79 | 80 | 81 | 82 | 83 | 84 |
| | Rate (kg/ha) | | | | | | | | | | | | | |
| Species | 0.3 | 0.3 | 0.3 | 0.3 | 0.3 | 0.3 | 0.3 | 0.3 | 0.3 | 0.3 | 0.25 | 0.25 | 0.3 | 0.25 |
| Soybean | 95 | 60 | 60 | 50 | 85 | 85 | 15 | 60 | 70 | 50 | 85 | 70 | 50 | 95 |
| Wheat | 100 | 100 | 100 | 85 | 50 | 50 | 20 | 50 | 70 | 85 | 95 | 70 | 15 | 20 |
| Corn | 100 | 100 | 100 | 95 | 80 | 60 | 50 | 80 | 100 | 100 | 100 | 80 | 70 | 50 |
| Velvetleaf | 100 | 100 | 100 | 100 | 100 | 100 | 95 | 100 | 80 | 100 | 100 | 95 | 40 | 30 |
| Morningglory | 100 | 100 | 100 | 100 | 100 | 100 | 100 | 100 | 100 | 100 | 100 | 100 | 40 | 80 |
| Chickweed | 100 | 100 | 100 | 90 | 100 | 100 | — | 100 | 0 | 90 | — | 90 | 10 | 15 |
| Cocklebur | 100 | 100 | 100 | 90 | 100 | 60 | 90 | 100 | 90 | 90 | 80 | 85 | 60 | 85 |
| Blackgrass | 80 | 85 | 100 | 95 | 80 | 100 | 10 | 20 | 15 | 40 | 95 | 90 | 5 | 0 |
| Green foxtail | 100 | 100 | 100 | 90 | 100 | 100 | 10 | 95 | 70 | 100 | 100 | 100 | 85 | 60 |
| Johnsongrass | 100 | 100 | 95 | 70 | 95 | 85 | 20 | 85 | 85 | 90 | 85 | 80 | 40 | 50 |

I claim:

1. A herbicidal compound of the formula

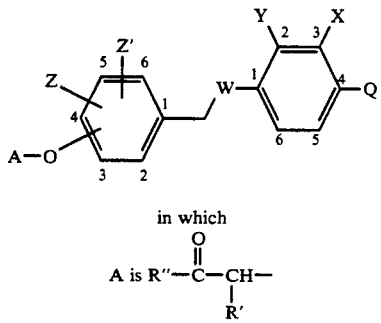

in which

A is R''—C(=O)—CH(R')—

Q is 4-difluoromethyl-4,5-dihydro-3-methyl-1,2,4-triazol-5(1H)-on-1-yl;

R is hydrogen, M, lower alkyl, cycloalkyl, lower alkenyl or lower alkynyl, or —[CHR$^7$(CH$_2$)$_m$O]$_n$R$^8$, R' is hydrogen or methyl;

R'' is —OR or amino, phenylamino, lower alkylamino, lower alkenylamino, lower alkoxyamino, cyano, or lower alkyl-, lower haloalkyl-, or phenylsulfonylamino of the formula —N(lower alkyl)-SO$_2$R$^9$ or —NHSO$_2$R$^9$;

R$^7$ is H or CH$_3$;

R$^8$ is lower alkyl;

R$^9$ is lower alkyl, lower haloalkyl, or phenyl;

X is hydrogen, fluorine, or chlorine;

Y is hydrogen;

W is oxygen or sulfur;

Z is hydrogen, fluorine, chlorine, bromine, lower alkyl, or methoxy;

Z' is hydrogen, fluorine, or chlorine;

m is 0 to 2, and n is 1 to 6;

M is sodium, potassium or ammonium; and the group AO— may be in the 2, 3, or 4-position of the phenyl ring.

2. A compound of claim 1 in which R'' is —OR; X is fluorine or chlorine; and Z is chlorine or lower alkyl.

3. A compound of claim 2 in which
R is lower alkyl or —[CHR$^7$(CH$_2$)$_m$O]$_n$R$^8$;
R' is methyl;
Z is in the 4-position;
Z' is hydrogen or chlorine in the 3-position;
m is 0 or 1, and n is 1 to 3; and
the group AO— is in the 2-position of the phenyl ring.

4. A compound of claim 3 in which Q is 4-difluoromethyl-4,5-dihydro-3-methyl-1,2,4-triazol-5(1H)-on-1-yl, R is methyl or CH$_3$O(CH$_2$)$_2$—O—(CH$_2$)$_2$—; and X is fluorine.

5. A compound of claim 4 in which W is oxygen and Z' is hydrogen.

6. The compound of claim 5 in which R is methyl, and Z is ethyl.

7. The compound of claim 5 in which R is methyl, and Z is 2-methylethyl.

8. The compound of claim 5 in which R and Z are each methyl.

9. The compound of claim 5 in which R is methyl, and Z is chlorine.

10. The compound of claim 5 in which R is 2-(2-methoxyethoxy)ethyl, and Z is methyl.

11. The compound of claim 4 in which R and Z are each methyl, W is sulfur, and Z' is hydrogen.

12. A herbicidal composition containing a herbicidally effective amount of a compound of claim 1 in admixture with an agriculturally acceptable carrier.

13. A method of controlling undesired plant growth that comprises applying to the locus where the undesired plants are growing, or are expected to grow, a herbicidally effective amount of a composition of claim 12.

* * * * *